(12) United States Patent
Batt

(10) Patent No.: US 8,759,390 B2
(45) Date of Patent: Jun. 24, 2014

(54) CHROMENE MODULATORS OF CHEMOKINE RECEPTOR ACTIVITY

(75) Inventor: Douglas G. Batt, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 578 days.

(21) Appl. No.: 13/003,777

(22) PCT Filed: Jul. 14, 2009

(86) PCT No.: PCT/US2009/050450
§ 371 (c)(1),
(2), (4) Date: Jan. 12, 2011

(87) PCT Pub. No.: WO2010/009069
PCT Pub. Date: Jan. 21, 2010

(65) Prior Publication Data
US 2011/0112146 A1    May 12, 2011

Related U.S. Application Data

(60) Provisional application No. 61/081,194, filed on Jul. 16, 2008.

(51) Int. Cl.
*C07D 311/60* (2006.01)
*A61K 31/35* (2006.01)

(52) U.S. Cl.
CPC .................................. *C07D 311/60* (2013.01)
USPC ........................................ 514/456; 549/405

(58) Field of Classification Search
CPC ................................................... C07D 311/60
USPC .................................. 549/389, 405; 514/456
See application file for complete search history.

(56) References Cited

U.S. PATENT DOCUMENTS 6,218,427 B1 *  4/2001  Ishizuka et al. ............... 514/456
6,479,671 B1    11/2002  Konoike et al.

FOREIGN PATENT DOCUMENTS

WO     WO 99/46991       9/1999
WO     WO 2004/110376    12/2004

OTHER PUBLICATIONS

Abbadie, C. et al., "Impaired neuropathic pain responses in mice lacking the chemokine receptor CCR2", Proceedings of the National Academy of Sciences, vol. 100, No. 13, pp. 7947-7952 (2003).
Abdi, R. et al., "Differential Role of CCR2 in Islet and Heart Allograft Rejection: Tissue Specificity of Chemokine/Chemokine Receptor Function In Vivo", The Journal of Immunology, vol. 172, pp. 767-775 (2004).
Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1+ Lymphocyte-Associated Th2-Type Immune Response in the Intestine", The Journal of Immunology, vol. 164, pp. 6303-6312 (2000).
Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).
Baba, M. et al., "Identification of CCR6, the Specific Receptor for a Novel Lymphocyte-directed CC Chemokine Larc", The Journal of Biological Chemistry, vol. 272, No. 23, pp. 14893-14898 (1997).
Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).
Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).
Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).
Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).
Carter, P.H., "Chemokine receptor antagonism as an approach to anti-inflammatory therapy: 'just right' or plain wrong?", Current Opinion in Chemical Biology, vol. 6, pp. 510-525 (2002).

(Continued)

*Primary Examiner* — Noble Jarrell
*Assistant Examiner* — Valerie Rodriguez-Garcia
(74) *Attorney, Agent, or Firm* — Laurelee A. Duncan

(57) ABSTRACT

The present application describes modulators of MCP-1 or CCR-2 of formula (I) or stereoisomers or prodrugs or pharmaceutically acceptable salts thereof, wherein $W^1$, $W^2$, $W^3$, Y, Z, $R^2$, $R^3$, $R^{3'}$ and $R^4$, are defined in the specification. In addition, methods of treating and preventing inflammatory diseases such as asthma and allergic diseases, as well as autoimmune pathologies such as rheumatoid arthritis and transplant rejection using modulators of formula (I) are disclosed.

(I)

8 Claims, No Drawings

(56) References Cited

OTHER PUBLICATIONS

Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).
Charo, I.F. et al., "The Many Roles of Chemokines and Chemokine Receptors in Inflammation", The New England Journal of Medicine, vol. 354, No. 6, pp. 610-621 (2006).
Cheng, J.-F. et al., "Novel Chromene Derivatives as TNF-α Inhibitors", Bioorganic & Medicinal Chemistry Letters, vol. 13, pp. 3647-3650 (2003).
Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).
Combadiere, C. et al., "Cloning and Functional Expression of a Human Eosinophil CC Chemokine Receptor", The Journal of Biological Chemistry, vol. 270, No. 27, pp. 16491-16494 (1995).
Connor, R.I. et al., "Change in Coreceptor Use Correlates with Disease Progression in HIV-1-Infected Individuals", J. Exp. Med., vol. 185, No. 4, pp. 621-628 (1997).
Connor, S.J. et al., "CCR2 expressing CD4+ lymphocytes are preferentially recruited to the ileum in Crohn's disease", Gut, vol. 53, pp. 1287-1294 (2004).
Conti, I. et al., "CCL2 (monocyte chemoattractant protein-1) and cancer", Seminars in Cancer Biology, vol. 14, pp. 149-154 (2004).
Craig, M.J. et al., "CCL2 (Monocyte Chemoattractant Protein-1) in cancer bone metastases", Cancer Metastasis Rev., vol. 25, pp. 611-619 (2006).
Dawson, J. et al., "Targeting monocyte chemoattractant protein-1 signalling in disease", Expert Opin. Ther. Targets, vol. 7, No. 1, pp. 35-48 (2003).
Deleuran, M. et al., "Localization of monocyte chemotactic and activating factor (MCAF/MCP-1) in psoriasis", Journal of Dermatological Science, vol. 13, pp. 228-236 (1996).
Dimitrijevic, O.B. et al., "Absence of the Chemokine Receptor CCR2 Protects Against Cerebral Ischemia/Reperfusion Injury in Mice", Stroke, vol. 38, pp. 1345-1353 (2007).
Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).
Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).
Feria, M. et al., "The CCR2 receptor as a therapeutic target", Expert Opin. Ther. Patents, vol. 16, No. 1, pp. 49-57 (2006).
Ferreira, A.M. et al., "Diminished Induction of Skin Fibrosis in Mice with MCP-1 Deficiency", Journal of Investigative Dermatology, vol. 126, pp. 1900-1908 (2006).
Frangogiannis, N.G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).
Gao, Z. et al., "Unraveling the Chemistry of Chemokine Receptor Ligands", Chemical Reviews, vol. 103, No. 9, pp. 3733-3752 (2003).
Gharaee-Kermani, M. et al., "Cc-chemokine receptor 2 required for bleomycin-induced pulmonary fibrosis", Cytokine, vol. 24, pp. 266-276 (2003).
Giles, R. et al., "Can We Target the Chemokine Network for Cancer Therapeutics?", Current Cancer Drug Targets, vol. 6, No. 8, pp. 659-670 (2006).
Gillitzer, R. et al., "MCP-1 mRNA Expression in Basal Keratinocytes of Psoriatic Lesions", The Journal of Investigative Dermatology, vol. 101, No. 2, pp. 127-131 (1993).
Gonzalo, J.-A. et al., "The Coordinated Action of CC Chemokines in the Lung Orchestrates Allergic Inflammation and Airway Hyper-responsiveness", J. Exp. Med., vol. 188, No. 1, pp. 157-167 (1998).
Grimm, M.C. et al., "Enhanced expression and production of monocyte chemoattractant protein-1 in inflammatory bowel disease mucosa", Journal of Leukocyte Biology, vol. 59, pp. 804-812 (1996).
Hasegawa, H. et al., "Antagonist of Monocyte Chemoattractant Protein 1 Ameliorates the Initiation and Progression of Lupus Nephritis and Renal Vasculitis in MRL/lpr Mice", Arthritis & Rheumatism, vol. 48, No. 9, pp. 2555-2566 (2003).
Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).
Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).
Horuk, R., "Molecular properties of the chemokine receptor family", Trends in Pharmacological Sciences, vol. 15, pp. 159-165 (1994).
Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).
Hughes, P.M. et al., "Monocyte Chemoattractant Protein-1 Deficiency is Protective in a Murine Stroke Model", Journal of Cerebral Blood Flow & Metabolism, vol. 22, No. 3, pp. 308-317 (2002).
Ishizuka, N. et al., "Structure-Activity Relationships of a Novel Class of Endothelin-A Receptor Antagonists and Discovery of Potent and Selective Receptor Antagonist, 2-(Benzo[1,3]dioxo1-5-yl)-6-isopropyloxy-4-(4-methoxyphenyl)-2H-chromene-3-carboxylic acid (S-1255). 1. Study on Structure-Activity Relationships and Basic Structure Crucial for $ET_A$ Antagonism", Journal of Medicinal Chemistry, vol. 45, No. 10, pp. 2041-2055 (2002).
Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).
Karpus, W.J. et al., "An Important Role for the Chemokine Macrophage Inflammatory Protein-1α in the Pathogenesis of the T Cell-Mediated Autoimmune Disease, Experimental Autoimmune Encephalomyelitis", The Journal of Immunology, vol. 155, pp. 5003-5010 (1995).
Karrer, S. et al., "The -2518 Promotor Polymorphism in the MCP-1 Gene is Associated with Systemic Sclerosis", The Journal of Investigative Dermatology, vol. 124, vol. 1, pp. 92-98 (2005).
Kasama, T. et al., "Interleukin-10 Expression and Chemokine Regulation During the Evolution of Murine Type II Collagen-Induced Arthritis", J. Clin. Invest., vol. 95, pp. 2868-2876 (1995).
Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).
Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).
Kim, W.J.H. et al., "MCP-1 deficiency is associated with reduced intimal hyperplasia after arterial injury", Biochemical and Biophysical Research Communications, vol. 310, pp. 936-942 (2003).
Kitagawa, K. et al., "Blockade of CCR2 Ameliorates Progressive Fibrosis in Kidney", American Journal of Pathology, vol. 165, No. 1, pp. 237-246 (2004).
Koch, A.E. et al., "Macrophage Inflammatory Protein-1α. A Novel Chemotactic Cytokine for Macrophages in Rheumatoid Arthritis", J. Clin. Invest., vol. 93, pp. 921-928 (1994).
Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).
Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).
Lee, I. et al., "Blocking the Monocyte Chemoattractant Protein-1/CCR2 Chemokine Pathway Induces Permanent Survival of Islet

(56) References Cited

OTHER PUBLICATIONS

Allografts through a Programmed Death-1 Ligand-1-Dependent Mechanism", The Journal of Immunology, vol. 171, pp. 6929-6935 (2003).

Lee, S.C. et al., "Cutaneous Injection of Human Subjects with Macrophage Inflammatory Protein-1α Induces Significant Recruitment of Neutrophils and Monocytes", vol. 164, pp. 3392-3401 (2000).

Liu, T. et al., "Depletion of macrophages reduces axonal degeneration and hyperalgesia following nerve injury", Pain, vol. 86, pp. 25-32 (2000).

Lloyd, C.M. et al., "RANTES and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and Invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of TER1, a Chemokine Receptor-Like Gene Expressed by Lymphoid Tissues", The Journal of Immunology, vol. 157, pp. 2759-2763 (1996).

Neote, K. et al., "Molecular Cloning, Functional Expression, and Signaling Characteristics of a C-C Chemokine Receptor", Cell, vol. 72, pp. 415-425 (1993).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pease, J.E. et al., "CCR1 antagonists in clinical development", Expert Opin. Investig. Drugs, vol. 14, No. 7, pp. 785-796 (2005).

Pérez de Lema, G. et al., "Chemokine Receptor Ccr2 Deficiency Reduces Renal Disease and Prolongs Survival in MRL/lpr Lupus-Prone Mice", Journal of the American Society of Nephrology, vol. 16, pp. 3592-3601 (2005).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rollins, B.J., "Chemokines", Blood, vol. 90, No. 3, pp. 909-928 (1997).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samson, M. et al., "Molecular Cloning and Functional Expression of a New Human CC-Chemokine Receptor Gene", Biochemistry, vol. 35, No. 11, pp. 3362-3367 (1996).

Saunders, J. et al., "Opportunities for novel therapeutic agents acting at chemokine receptors", Drug Discovery Today, vol. 4, No. 2, pp. 80-92 (1999).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 and online data supplement (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/lpr mice", Rheumatology, vol. 43, pp. 1121-1128 (2004).

Smith, M.W. et al., "Contrasting Genetic Influence of CCR2 and CCR5 Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-$Fas^{lpr}$ Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Wells, T.N.C. et al., "Plagiarism of the host immune system: lessons about chemokine immunology from viruses", Current Opinion in Biotechnology, vol. 8, pp. 741-748 (1997).

(56) References Cited

OTHER PUBLICATIONS

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshie, O. et al., "Novel lymphocyte-specific CC chemokines and their receptors", Journal of Leukocyte Biology, vol. 62, pp. 634-644 (1997).

Zlotnik, A. et al., "Chemokines: A New Classification System and Their Role in Immunity", Immunity, vol. 12, pp. 127-127 (2000).

* cited by examiner

CHROMENE MODULATORS OF CHEMOKINE RECEPTOR ACTIVITY

CROSS-REFERENCE TO RELATED APPLICATION

This application claims priority benefit to U.S. Provisional Application Ser. No. 61/081,194, filed on Jul. 16, 2008, the contents of which are herein incorporated by reference in its entirety.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity* 2000, 12, 121): CCR-1 (or "CKR-1" or "CC-CKR-1") [MIP-1α, MCP-3, MCP-4, RANTES] (Neote et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Samson et al., *Biochemistry* 1996, 35, 3362-3367); CCR-6 (or "CKR-6" or "CC-CKR-6") [LARC] (Baba et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., *J. Immunol.,* 1996, 157, 2759-2763); CCR-10 (or "CKR-10" or "CC-CKR-10") [MCP-1, MCP-3] (Bonini et al., *DNA Cell Biol.* 1997, 16, 1249-1256); and CCR-11 [MCP-1, MCP-2, and MCP-4] (Schweickart et al., *J. Biol. Chem.* 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., *Curr. Opin. Chem. Biol.* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-la binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo et al., *New Eng. J. Med.* 2006, 354, 610-621; Gao, Z. et al., *Chem. Rev.* 2003, 103, 3733; Carter, P. H., *Curr. Opin. Chem. Biol.* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1–/– mice were unable to recruit monocytes into sites of inflammation after several different types of immune challenge (Lu, B. et al., *J. Exp. Med.* 1998, 187, 601). Likewise, CCR-2–/– mice were unable to recruit monocytes or produce interferon-γ when challenged with various exogenous agents; moreover, the leukocytes of CCR-2 null mice did not migrate in response to MCP-1 (Boring, L. et al., *J. Clin. Invest.* 1997, 100, 2552), thereby demonstrating the specificity of the MCP-1/CCR-2 interaction. Two other groups have independently reported equivalent results with different strains of CCR-2–/– mice (Kuziel, W. A. et al., *Proc. Natl. Acad. Sci. USA* 1997, 94, 12053, and Kurihara, T. et al., *J. Exp. Med.* 1997, 186, 1757). The viability and generally normal health of the MCP-1–/– and CCR-2–/– animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: Feria, M. et al., *Exp. Opin. Ther. Patents* 2006, 16, 49; and Dawson, J. et al., *Exp. Opin. Ther. Targets* 2003, 7, 35). This hypothesis has now been validated in a number of different animal disease models, as described below.

It is known that MIP-1α is elevated in the synovial fluid and blood of patients with rheumatoid arthritis (Koch, A. et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. et al., *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It is known that MCP-1 is upregulated in patients who develop bronchiolitis obliterans syndrome after lung transplantation (Reynaud-Gaubert, M. et al., *J. Heart Lung Transplant.*, 2002, 21, 721-730; Belperio, J. et al., *J. Clin. Invest.* 2001, 108, 547-556). In a murine model of bronchiolitis obliterans syndrome, administration of an antibody to MCP-1 led to attenuation of airway obliteration; likewise, CCR2–/– mice were resistant to airway obliteration in this same model (Belperio, J. et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (Lee, I. et al. *J. Immunol.* 2003, 171, 6929; Abdi, R. et al., *J. Immunol.* 2004, 172, 767). In rat graft models, CCR2 and MCP-1 was shown to be upregulated in grafts that develop graft vasculopathy (Horiguchi, K. et al., *J. Heart Lung Transplant.* 2002, 21, 1090). In another study, anti-MCP-1 gene therapy attenuated graft vasculopathy (Saiura, A. et al., *Arterioscler. Thromb. Vasc. Biol.* 2004, 24, 1886). One study described inhibition of experimental vein graft neoinitimal formation by blockage of MCP-1 (Tatewaki, H. et al., *J. Vasc. Surg.* 2007, 45,1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Gonzalo, J-A., et al., *J. Exp. Med.* 1998, 188, 157). It proved possible to reduce allergic airway inflammation in *Schistosoma mansoni* egg-challenged mice through the administration of antibodies for MCP-1 (Lukacs, N. W. et al., *J. Immunol.* 1997, 158, 4398). Consistent with this, MCP-1–/– mice displayed a reduced response to challenge with *Schistosoma mansoni* egg (Lu, B. et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Lloyd, C. M. et al., *J. Exp. Med.* 1997, 185, 1371). In addition, MCP-1–/– mice with induced nephrotoxic serum nephritis showed significantly less tubular damage than their MCP-1+/+ counterparts (Tesch, G. H. et al., *J. Clin. Invest.* 1999, 103, 73).

Several studies have demonstrated the potential therapeutic value of antagonism of the MCP-1/CCR2 interaction in treating systemic lupus erythematosus. CCR2–/– mice exhibited prolonged survival and reduced renal disease relative to their WT counterparts in a murine model of systemic lupus erythematosus (Perez de Lema, G. et al., *J. Am. Soc. Neph.* 2005, 16, 3592). These data are consistent with the disease-modifying activity found in recent studies on genetic deletion of MCP-1 (Shimizu, S. et al., *Rheumatology (Oxford)* 2004, 43, 1121; Tesch, G. H. et al., *J. Exp. Med.* 1999, 190, 1813) or administration of a peptide antagonist of CCR2 (Hasegawa, H. et al., *Arthritis & Rheumatism* 2003, 48, 2555) in rodent models of lupus.

A remarkable 30-fold increase in CCR2$^+$ lamina propria lymphocytes was observed in the small bowels from Crohn's patients relative to non-diseased ileum (Connor, S. J. et al., *Gut* 2004, 53, 1287). Also of note, there was an expansion in the subset of circulating CCR2$^+$/CD14$^+$/CD56$^+$ monocytes in patients with active Crohn's disease relative to controls. Several rodent studies have demonstrated the potential therapeutic value of antagonism of the MCP-1/CCR2 interaction in treating Crohn's disease/colitis. CCR-2–/– mice were protected from the effects of dextran sodium sulfate-induced colitis (Andres, P. G. et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (Tokuyama, H. et al., *Int. Immunol.* 2005, 17, 1023). Finally, MCP-1–/– mice showed substantially reduced colonic damage (both macroscopic and histological) in a hapten-induced model of colitis (Khan, W. I. et al., *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (Reinecker, H. C. et al., *Gastroenterology* 1995, 108, 40, and Grimm, M. C. et al., *J. Leukoc. Biol.* 1996, 59, 804).

One study described the association of promoter polymorphism in the MCP-1 gene with scleroderma (systemic sclerosis) (Karrer, S. et al., *J. Invest. Dermatol.* 2005, 124, 92). In related models of tissue fibrosis, inhibition of CCR2/MCP-1 axis reduced fibrosis in skin (Yamamoto, T. et al., *J. Invest. Dermatol.* 2003, 121, 510; Ferreira, A. M. et al., *J. Invest. Dermatol.* 2006, 126, 1900), lung (Okuma, T. et al., *J. Pathol.* 2004, 204, 594; Gharaee-Kermani, M. et al., *Cytokine* 2003, 24, 266), kidney (Kitagawa, K. et al., *Am. J. Pathol.* 2004, 165, 237; Wada, T. et al., *J. Am. Soc. Nephrol.* 2004, 15, 940), heart (Hayashidani, S. et al., *Circulation* 2003, 108, 2134), and liver (Tsuruta, S. et al., *Int. J. Mol. Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Jones, M. L. et al., *J. Immunol.* 1992, 149, 2147).

Several studies have shown the potential therapeutic value of antagonism of the MCP-1/CCR2 interaction in treating cancer (reviewed in: Craig, M. J. et al., *Cancer Metastasis Rev.* 2006, 25, 611; Conti, I. et al., *Seminars in Cancer Biology* 2004, 14, 149; Giles, R. et al., *Curr. Cancer Drug Targets* 2006, 6, 659). When immunodeficient mice bearing human breast carcinoma cells were treated with an anti-MCP-1 antibody, inhibition of lung micrometastases and increases in survival were observed (Salcedo, R. et al., *Blood* 2000, 96, 34-40). Using human clinical tumor specimens, CCR2 expression was associated with prostrate cancer progression (Lu, Y. et al., *J. Cell. Biochem.* 2007, 101, 676). In vitro, MCP-1 expression has been shown to mediate prostrate cancer cell growth and invasion (Lu, Y. et al., *Prostate* 2006, 66, 1311); furthermore, MCP-1 expressed by prostate cancer cells induced human bone marrow progenitors for bone resorption (Lu, Y. et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (Cipollone, F. et al. *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Roque, M. et al. *Arterioscler. Thromb. Vasc. Biol.* 2002, 22, 554; Schober, A. et al. *Circ. Res.* 2004, 95, 1125; Kim, W. J. et al., *Biochem. Biophys. Res. Commun.* 2003, 310, 936). In mice, transfection of a dominant negative inhibitor of MCP-1 in the skeletal muscle (Egashira, K. et al., *Circ. Res.* 2002, 90, 1167) also reduced intimal hyperplasia after arterial injury. Blockade of CCR2 using a neutralizing antibody reduced neointimal hyperplasia after stenting in primates (Horvath, C. et al., *Circ. Res.* 2002, 90, 488).

Two reports describe the overexpression of MCP-1 rats with induced brain trauma (King, J. S. et al., *J. Neuroimmunol.* 1994, 56, 127, and Berman, J. W. et al., *J. Immunol.* 1996, 156, 3017). In addition, studies have shown that both CCR2–/– (Dimitrijevic, O. B. et al., *Stroke* 2007, 38, 1345) and MCP-1–/– mice (Hughes, P. M. et al., *J. Cereb. Blood Flow Metab.* 2002, 22, 308) are partially protected from ischemia/reperfusion injury.

It is known that monocytes/macrophages play an important role in the development of neuropathic pain (Liu, T. et al., *Pain* 2000, 86, 25). Consistent with this notion, a potential role for CCR2 in the treatment of both inflammatory and neuropathic pain has been described recently. CCR2–/– mice showed altered responses to inflammatory pain relative to their WT counterparts, including reduced pain behavior after intraplantar formalin injection and slightly reduced mechanical allodynia after intraplantar CFA injection (Abbadie, C. et al., *Proc. Natl. Acad. Sci., USA* 2003, 100, 7947). In addition, CCR2–/– mice did not display significant mechanical allodynia after sciatic nerve injury. Likewise, a small molecule CCR2 antagonist reduced mechanical allodynia to ~80% of pre-injury levels after oral administration (Abbadie, C. et al., WO 2004/110376).

One study described the critical role of MCP-1 in ischemic cardiomyopathy (Frangogiannis, N.G. et al., *Circulation* 2007, 115, 584). Another study described the attenuation of experimental heart failure following inhibition of MCP-1 (Hayashidani, S. et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Russell, M. E. et al., *Proc. Natl. Acad. Sci. USA* 1993, 90, 6086). The overexpression of MCP-1 has been noted in the lung endothelial cells of patients with idiopathic pulmonary fibrosis (Antoniades, H. N. et al., *Proc. Natl. Acad. Sci. USA* 1992, 89, 5371). Similarly, the overexpression of MCP-1 has been noted in the skin from patients with psoriasis (Deleuran, M. et al., *J. Dermatol. Sci.* 1996, 13, 228, and Gillitzer, R. et al., *J. Invest. Dermatol.* 1993, 101, 127); correlative findings with predominance of CCR2+ cells have also been reported (Vestergaard, C. et al., *Acta Derm. Venerol.* 2004, 84, 353). Finally, a recent report has shown that MCP-1 is overexpressed in the brains and cerebrospinal fluid of patients with HIV-1-associated dementia (Garzino-Demo, A., WO 99/46991).

In addition, CCR2 polymorphism has been shown to be associated with sarcoidosis at least in one subset of patients (Spagnolo, P. et al., *Am. J. Respir. Grit. Care Med.* 2003, 168, 1162).

It should also be noted that CCR-2 has been implicated as a co-receptor for some strains of HIV (Doranz, B. J. et al., *Cell* 1996, 85, 1149). It has also been determined that the use of CCR-2 as an HIV co-receptor can be correlated with disease progression (Connor, R. I. et al., *J. Exp. Med.* 1997, 185, 621). This finding is consistent with the recent finding that the presence of a CCR-2 mutant, CCR2-64I, is positively correlated with delayed onset of HIV in the human population (Smith, M. W. et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng. J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 or CCR-2 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel chromene derivatives for use in therapy.

The present invention provides the use of novel chromene derivatives for the manufacture of a medicament for the treatment of inflammatory diseases.

These and other features of the invention, which will become apparent during the following detailed description, have been achieved by the inventors' discovery that compounds of formula (I):

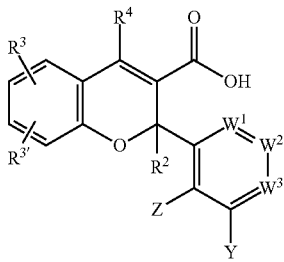

(I)

or stereoisomers or prodrugs or pharmaceutically acceptable salts thereof, wherein $W^1$, $W^2$, $W^3$, Y, Z, $R^2$, $R^3$, $R^{3'}$ and $R^4$, are defined below, are effective modulators of MCP-1 and chemokine activity.

DETAILED DESCRIPTION OF THE PRESENT INVENTION

In one embodiment, the present invention provides novel compounds of formula (I):

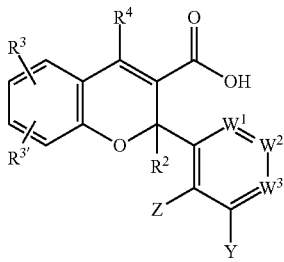

(I)

or a stereoisomer or a pharmaceutically acceptable salt thereof, wherein:
$R^2$ is H, or $C_{1-4}$ alkyl;
$R^3$ and $R^{3'}$ are independently H, $C_{1-4}$ alkyl, $C_{1-4}$ alkoxy, halo, or halo$C_{1-4}$ alkyl;
or $R^3$ and $R^{3'}$, when attached to neighboring carbons, taken together form —CH=CH—CH=CH—;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, $C_{1-4}$ alkoxy, halo or halo$C_{1-4}$ alkyl;
Y and Y' are independently H, $C_{1-4}$ alkyl, $C_{1-4}$ alkoxy, halo, halo$C_{1-4}$ alkyl or $NO_2$;
Z and Z' are independently H or halo;
or Y and Z, Y' and Z', Y and X, or Y' and X are taken together to form —CH=CH—CH=CH—;
or Y and X or Y' and X are taken together to form —O—CH₂—O—; provided that:
(1) only one of $W^1$, $W^2$ or $W^3$ may be N;
(2) if $W^2$ is N, then X, Y, Z and Z' are not all H;
(3) if $W^3$ is N, then $W^1$ and $W^2$ are both CH and Y and Z are H;
(4) if $W^1$, $W^2$ and $W^3$ are all CH, then Y cannot be H;
(5) if Y is $C_{1-4}$alkoxy then X is not H;
(6) if $W^1$, $W^2$ and $W^3$ are all CH and Z is Cl, then Y is Cl; and
(7) if X is F then one of Y or Y' is not H.

In yet another embodiment, compounds of the present invention, or a stereoisomer or pharmaceutically acceptable salt from thereof, are those in which:
$R^2$ is H, or $C_{1-4}$ alkyl;
$R^3$ and $R^{3'}$ are independently H, $C_{1-4}$ alkyl, $C_{1-4}$ alkoxy, halo, or halo$C_{1-4}$ alkyl;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, $C_{1-4}$ alkoxy, halo or halo$C_{1-4}$ alkyl;
Y and Y' are independently H, $C_{1-4}$ alkyl, $C_{1-4}$ alkoxy, halo, halo$C_{1-4}$ alkyl or $NO_2$;
Z and Z' are independently H or halo;
or Y and Z, Y' and Z', Y and X, or Y' and X are taken together to form —CH=CH—CH=CH—;
or Y and X or Y' and X are taken together to form —O—CH₂—O—.

In still yet another embodiment, compounds of the present invention, or a stereoisomer or pharmaceutically acceptable salt from thereof, are those in which:
$R^2$ is H, or $C_{1-4}$ alkyl;
$R^3$ and $R^{3'}$ are independently H, $C_{1-4}$ alkyl, $C_{1-4}$ alkoxy, halo, or halo$C_{1-4}$ alkyl;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, $C_{1-4}$ alkoxy, halo or halo$C_{1-4}$ alkyl;
Y and Y' are independently H, $C_{1-4}$ alkyl, $C_{1-4}$ alkoxy, halo, halo$C_{1-4}$ alkyl or $NO_2$;
Z and Z' are independently H or halo;
or Y and Z, Y' and Z', Y and X, or Y' and X are taken together to form —CH=CH—CH=CH—.

In one embodiment, compounds of the present invention, or a stereoisomer or pharmaceutically acceptable salt from thereof, are those in which:
$R^2$ is H, or $C_{1-4}$ alkyl;
$R^3$ and $R^{3'}$ are independently H, $C_{1-4}$ alkyl, $C_{1-4}$ alkoxy, halo, or halo$C_{1-4}$ alkyl;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, $C_{1-4}$ alkoxy, halo or halo$C_{1-4}$ alkyl;
Y and Y' are independently H, $C_{1-4}$ alkyl, $C_{1-4}$ alkoxy, halo, halo$C_{1-4}$ alkyl or $NO_2$; and
Z and Z' are independently H or halo.

In another embodiment, compounds of the present invention, or a stereoisomer or pharmaceutically acceptable salt from thereof, are those in which:

$R^2$ is H, or $C_{1-4}$ alkyl;
$R^3$ and $R^{3'}$ are independently H, $C_{1-4}$ alkyl, $C_{1-4}$ alkoxy, or halo;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, $C_{1-4}$ alkoxy, halo or halo$C_{1-4}$ alkyl;
Y and Y' are independently H, $C_{1-4}$ alkyl, $C_{1-4}$ alkoxy, halo, or halo$C_{1-4}$ alkyl; and
Z and Z' are independently H or halo.

In yet another embodiment, compounds of the present invention, or a stereoisomer or pharmaceutically acceptable salt from thereof, are those in which:
$R^2$ is H, or $C_{1-4}$ alkyl;
$R^3$ and $R^{3'}$ are independently H, $C_{1-4}$ alkoxy, or halo;
$R^4$ is H or $C_{1-4}$ alkyl;
$W^1$ is N or C—Z';
$W^2$ is N or C—Y';
$W^3$ is N or C—X;
X is H, $C_{1-4}$ alkyl, halo or halo$C_{1-4}$ alkyl;
Y and Y' are independently H, $C_{1-4}$ alkyl, halo, or halo$C_{1-4}$ alkyl; and
Z and Z' are independently H or halo.

In still yet another embodiment, compounds of the present invention, or a stereoisomer or pharmaceutically acceptable salt from thereof, are those in which:
$R^2$ is H, or $C_{1-4}$ alkyl;
$R^3$ and $R^{3'}$ are independently H or halo;
$R^4$ is H or $C_{1-4}$ alkyl;
$W^1$ is N or C—Z';
$W^2$ is N or C—Y';
$W^3$ is N or C—X;
X is H, halo or halo$C_{1-4}$ alkyl;
Y and Y' are independently H, halo, or halo$C_{1-4}$ alkyl; and
Z and Z' are independently H or halo.

In one embodiment, compounds of the present invention, or a stereoisomer or pharmaceutically acceptable salt from thereof, are those in which:
$R^2$ is H, methyl or ethyl;
$R^3$ and $R^{3'}$ are H;
$R^4$ is H;
$W^1$ is N or C—Z';
$W^2$ is N or C—Y';
$W^3$ is N or C—X;
X is H, Br, Cl, F or $CF_3$;
Y and Y' are independently H, Br, Cl, F or $CF_3$; and
Z and Z' are independently H, Br, Cl or F.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-2 receptor activity comprising administering to a patient in need thereof a therapeutically effective amount of a compound of the present invention.

In another embodiment, the present invention is directed to a method for modulation of MCP-1 activity that is mediated by the CCR-2 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-2, comprising administering to a patient in need thereof a therapeutically effective amount of a compound of the present invention.

In another embodiment, the present invention is directed to a method for modulation of CCR2 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-2 receptor activity comprising administering to a patient in need thereof a therapeutically effective amount of a pharmaceutical composition comprised of a compound of the present invention and one or more active ingredients.

In yet another embodiment, the present invention is directed to a method for modulation of MCP-1 activity that is mediated by the CCR-2 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-2, comprising administering to a patient in need thereof a therapeutically effective amount of a pharmaceutical composition comprised of a compound of present invention and one or more active ingredients.

In another embodiment, the present invention is directed to a method for modulation of CCR-2 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

In another embodiment, the present invention provides a compound of the present invention for use in therapy for treating an inflammatory disease.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of an inflammatory disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of an inflammatory disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat an inflammatory disease.

The invention may be embodied in other specific forms without departing from the spirit or essential attributes thereof This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy* 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

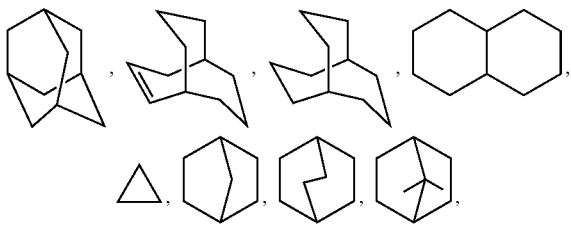

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

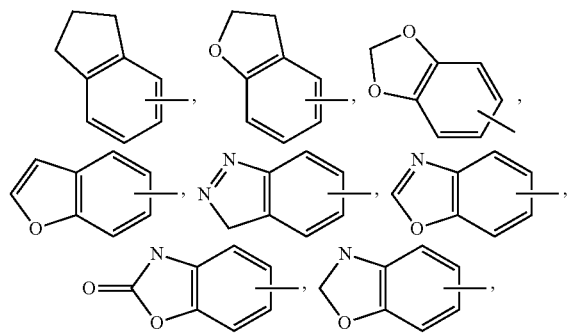

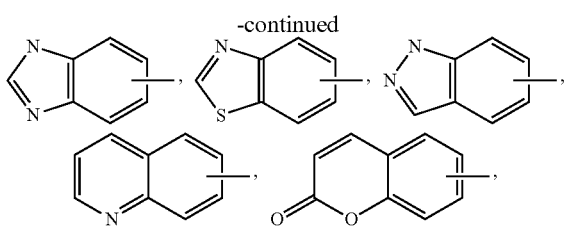

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, 13-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., p. 1418 (Mack Publishing Company, Easton, Pa., 1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters, carbamates and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Ch. 31 (Academic Press, 1996);

b) Bundgaard, H., ed., *Design of Prodrugs* (Elsevier, 1985);

c) Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, Ruffolo, Jr., R. R. et al., eds., pp. 173-198 (CRC Press, Inc., 1995); and d) Testa, B. et al., *Hydrolysis in Drug and Prodrug Metabolism* (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition (Wiley and Sons, 1999)).

Compounds of Formula (I) can be prepared by the route outlined in Scheme 1, wherein A represents the pendent ring of Formula (I). A phenolic β-ketoester 1-1 (where R is, for example, an alkyl group such as methyl, ethyl or tert-butyl) can be reacted with an aromatic aldehyde A-CHO in the presence of catalytic amounts of an acid such as acetic acid and a base such as piperidine in a solvent such as isopropanol to provide an intermediate 1-2 ($R^2$=H), for example as reported by Cheng, J. et al., *Bioorg. Med. Chem. Lett.* 2003, 13, 3647. Alternatively, an appropriate chromenone 1-3 (where R is, for example, an alkyl group such as methyl, ethyl or tert-butyl and $R^2$=H or alkyl) can be converted to 1-2 by treatment with a Grignard reagent A-MgBr or A-MgCl in the presence of a copper (I) compound such as copper(I) iodide, copper(I) bromide, or copper (I) cyanide, or by treatment with a lithium organocuprate $A_2$CuLi, for example as reported by N. Ishizuka et al., *J. Med. Chem.* 2002, 45, 2041, or by Saengchantara, S. et al., *Tetrahedron* 1990, 46, 3029.

Scheme 1

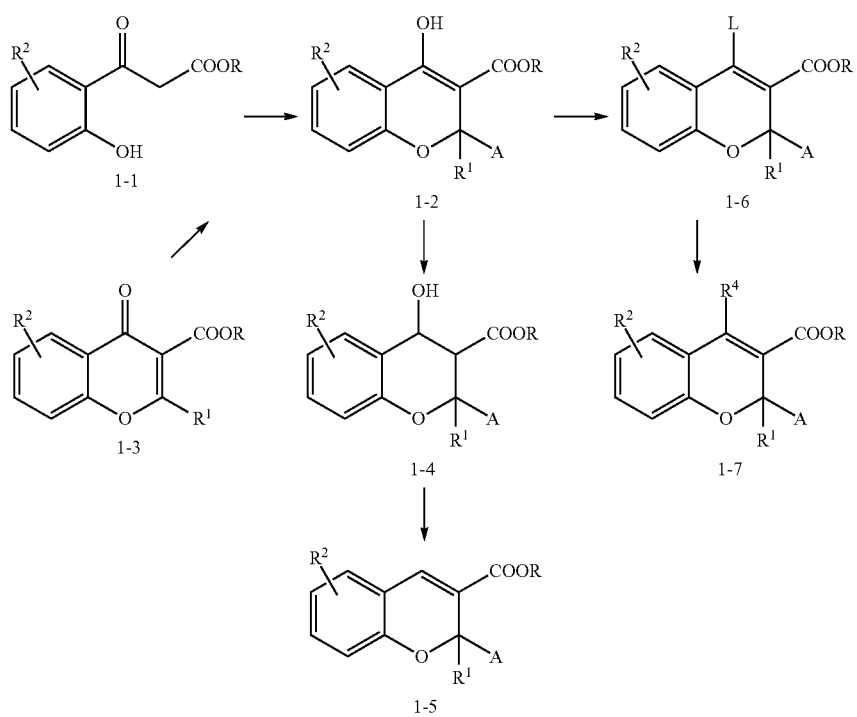

Intermediates 1-2 can be treated with a reducing agent such as sodium borohydride in an appropriate solvent such as methanol or a mixture of solvents such as methanol and tetrahydrofuran to provide intermediates 1-4. These intermediates can then be converted to intermediates 1-5 (where R is, for example, alkyl) by a number of methods known to one skilled in the art, for example by treatment with an acid, optionally in an appropriate solvent, for example trifluoroacetic acid or p-toluenesulfonic acid in toluene. Alternatively, the hydroxyl group of 1-4 can be converted into a more reactive leaving group such as a methanesulfonate ester, trifluoromethanesulfonate ester, arylsulfonate ester or halogen, using methods well known to one skilled in the art. This intermediate can then be treated with a base such as, for example, 1,8-diazabicyclo[5.4.0]undec-7-ene to induce elimination to 1-5. Intermediates 1-5 (R=alkyl) can then be converted to compounds of Formula (I) represented by 1-5 (R=H) by hydrolysis under basic or acidic conditions, or (for R=tert-butyl) by treatment with a strong acid such as trifluoroacetic acid, hydrochloric acid or p-toluenesulfonic acid, optionally in an appropriate solvent. Such conversions of esters to acids are well known by those skilled in the art of organic synthesis.

Intermediates 1-4 can also be converted directly to compounds of Formula (I) represented by 1-5 (R=H) by treatment with an aqueous solution of a base such as sodium hydroxide.

Intermediates 1-2 can also be converted to intermediates 1-7 wherein $R^4$ is alkyl using procedures well known in the chemical literature. Intermediates 1-2 can be converted into 1-6 wherein L is a group suitable for replacement with an alkyl moiety. For example, treatment of 1-2 with a base such as sodium hydride in a suitable solvent such as diethyl ether or tetrahydrofuran, followed by treatment of the resulting anion with a chlorophosphate such as dimethyl chlorophosphate or diethyl chlorophosphate (as reported by Sum et al., Can. J. Chem. 1979, 57, 1431), can provide the intermediates 1-6 where L is a dialkylphosphoryloxy group. Treatment of these intermediates with a lithium dialkylcuprate can provide the intermediates 1-7 (where $R^4$ is an alkyl group), which can then be converted to the compounds of Formula I represented by 1-7 (where $R^4$ is H), for example by hydrolysis with aqueous sodium or potassium hydroxide as described above.

The starting intermediates 1-1 and 1-3 in Scheme 1 can be prepared using methods reported in the chemical literature. For example, phenolic β-ketoesters 1-1 can be prepared by the base-catalyzed condensation of a 2'-hydroxyacetophenone with a dialkyl carbonate as reported by Cushman, M. et al., J. Med. Chem. 1991, 34, 798, or by condensation of a salicylic acid derivative with an acetate ester (using a procedure such as that reported by Appendino, G. et al., J. Nat. Prod. 1999, 62, 1627). Chromenone derivatives 1-3 can be prepared, for example, by the base-catalyzed condensation of a β-ketoester such as methyl acetoacetate with a 2-fluorobenzoyl chloride to provide 1-3 ($R^2$=R=methyl), as reported by G. Coppola et al., Synthesis 1981, 523, or by the treatment of a phenolic β-ketoester 1-1 with triethyl orthoformate and acetic anhydride or with acetic formic anhydride and sodium formate to provide 1-3 ($R^2$=H) as reported by Okumura, K. et al., Chem. Pharm. Bull. 1974, 22, 331.

EXAMPLES

Abbreviations used in the Examples are defined as "2×" for twice, "° C." for degrees Celsius, "g" for gram or grams, "mmol" for millimolar, "mL" for milliliter or milliliters, "µL" for microliter or microliters, "M" for molar, "min" for minute or minutes, "mg" for milligram or milligrams, "h" for hour or hours, "LC" for liquid chromatography, "HPLC" for high performance liquid chromatography, "TLC" for thin layer chromatography, "MS" for mass spectroscopy, "rt" or "RT" for room temperature, "calc." for calculated, "THF" for tetrahydrofuran, "CDCl$_3$" for chloroform, "sat." for saturated, "N" for normal, and "HCl" for hydrochloric acid. "D", "L", "R" and "S" are stereochemical designations familiar to those skilled in the art. Chemical names were derived using ChemDraw Ultra Version 9.0.5 (CambridgeSoft). When this program failed to provide a name for the exact structure in question, an appropriate name was assigned using the same methodology utilized by the program.

Example 1

Preparation of racemic
2-(3-chlorophenyl)-2H-chromene-3-carboxylic acid

Step 1. A mixture of methyl 3-(2-hydroxyphenyl)-3-oxopropanoate (prepared according to Cushman, M. et al., *J. Med. Chem.* 1991, 34, 798; 250 mg, 1.29 mmol) and 3-chlorobenzaldehyde (146 µL, 1.29 mmol) in isopropanol (5.0 mL) was treated with piperidine (13 µL, 129 µmol) and acetic acid (7.4 µL, 129 µmol) and heated to reflux for 17 h. After this time, the mixture was cooled to rt. The cooled solution was concentrated under vacuum and the resulting residue was purified by rotary TLC, eluting with 9:1 hexane-ethyl acetate, to provide a colorless gum. The colorless gum was crystallized from a hot isopropanol/water solution to provide methyl 2-(3-chlorophenyl)-4-oxochroman-3-carboxylate as an off-white solid (173 mg, 42%). The NMR indicated predominantly the enolic form. $^1$H NMR (400 MHz, CDCl$_3$) δ ppm 3.78 (s, 3 H) 6.21 (s, 1 H) 6.82 (d, J=8.1 Hz, 1 H) 6.97 (t, J=7.9 Hz, 1 H) 7.18-7.32 (m, 4 H) 7.34 (m, 1 H) 7.69 (dd, J=7.9, 1.8 Hz, 1 H) 12.28 (br. s, 1 H). High resolution mass spec (M+H)$^+$ calc. 317.0581, found 317.0597.

Step 2. A solution of methyl 2-(3-chlorophenyl)-4-oxochroman-3-carboxylate (153 mg, 483 µmol) in tetrahydrofuran (2.0 mL) was diluted with methanol (4.0 mL) and treated at rt with sodium borohydride (18 mg, 483 µmol). After 30 min, additional sodium borohydride (18 mg, 483 µmol) was added and stirring at rt was continued. After 3.5 h, additional sodium borohydride (18 mg, 483 µmol) was added. After 2 h, the mixture was concentrated under vacuum and stirred with water containing a few drops of 1.0 M NaOH (pH >10). The resulting mixture was extracted three times with ethyl acetate, and the combined organic phases were dried over sodium sulfate and concentrated under vacuum to yield a residue. The residue was taken up in methanol (2.0 mL) and 1.0 M aqueous sodium hydroxide (2.0 mL) and then heated to reflux for 4 h. The solution was cooled to rt and acidified with 3 mL of 1.0 M aqueous HCl. Methanol (about 10 mL) was added with heating until the gum all dissolved, then the solution was refrigerated. The resulting white crystals of Example 1 were isolated by filtration (39 mg, 28%). $^1$H NMR (400 MHz, CDCl$_3$) δ ppm 6.25 (s, 1 H) 6.81 (d, J=7.6 Hz, 1 H) 6.91 (dt, J=7.6, 1.0 Hz, 1 H) 7.16-7.25 (m, 4 H) 7.29 (dt, J=4.3, 2.0 Hz, 1 H) 7.37 (m, 1 H) 7.69 (s, 1 H). High resolution mass spectrum (M+H)$^+$ calc. 287.0475, found 287.0487.

Example 2-1

Preparation of racemic 2-(4-chloro-3-(trifluoromethyl)phenyl)-2H-chromene-3-carboxylic acid Step 1. A mixture of methyl 3-(2-hydroxyphenyl)-3-oxopropanoate (prepared according to Cushman, M. et al., *J. Med. Chem.* 1991, 200 mg, 1.03 mmol) and 4-chloro-3-(trifluoromethyl)benzaldehyde (148 µL, 1.03 mmol) in isopropanol (4.0 mL) was treated with piperidine (10 µL, 103 µmol) and acetic acid (5.9 µL, 103 µmol) and heated to reflux for 16.5 h. After this time, water (2.0 mL) was added and the solution was slowly cooled to rt, whereupon crystals formed. After standing at rt, the mixture was cooled on ice, and the resulting crystals were collected by filtration and dried to provide methyl 2-(4-chloro-3-(trifluoromethyl)phenyl)-4-oxochroman-3-carboxylate as a white crystalline solid (204 mg, 51%). A second crop (47 mg) was obtained from the mother liquor, raising the total yield to 63%. The NMR indicated predominantly the enolic form. $^1$H NMR (500 MHz, CDCl$_3$) δ ppm 3.79 (s, 3 H) 6.24 (s, 1 H) 6.82 (d, J=8.2 Hz, 1 H) 7.00 (t, J=7.7 Hz, 1 H) 7.31 (t, J=6.9 Hz, 1 H) 7.42 (m, 2 H) 7.70 (m, 2 H) 12.27 (br. s, 1 H). Mass spectrum m/z 407.19, 409.18 (M+Na)$^+$.

Step 2. A solution of methyl 2-(4-chloro-3-(trifluoromethyl)phenyl)-4-oxochroman-3-carboxylate (300 mg, 780 µmol) in tetrahydrofuran (2.0 mL) was diluted with methanol (4.0 mL, 780 µmol) and treated at rt with sodium borohydride (30 mg, 780 µmol). After 2.25 h, the solution was poured into water (about 25 mL), treated with 1.0 M aqueous HCl (about 1 mL) and then extracted three times with ethyl acetate. The combined organic phases were dried over sodium sulfate and concentrated under vacuum to provide crude racemic methyl 2-(4-chloro-3-(trifluoromethyl)phenyl)-4-hydroxychroman-3-carboxylate as a white solid (292 mg). Without further purification, this material was dissolved in dichloromethane (9.5 mL) and treated with trifluoroacetic acid (0.5 mL). After standing at rt for 1.5 h, the solution was washed with saturated aqueous sodium bicarbonate, dried over sodium sulfate and concentrated under vacuum to yield a residue. The residue was purified by column chromatography (silica gel, 2-10% ethyl acetate/hexane) to provide crude racemic methyl 2-(4-chloro-3-(trifluoromethyl)phenyl)-2H-chromene-3-carboxylate as a colorless gum (65 mg). Without further purification, a solution of a portion of this gum (60 mg) in methanol (2.0 mL) was treated with 1.0 M aqueous sodium hydroxide (2.0 mL) and heated at reflux for 4.5 h. After this time, the solution was cooled to rt. Once at the prescribed temperature, a white solid formed, which was removed by filtration and washed with water. The combined filtrate and wash were acidified with 1.0 M aqueous HCl, giving a gummy material. A small amount of methanol was added to the gummy material and the resulting mixture was heated briefly, then stirred while cooling to rt, thereby forming a white solid, which was collected by filtration, washed with water and dried under vacuum to provide Example 2-1 (29 mg). $^1$H NMR (400 MHz, CDCl$_3$) δ ppm 6.26 (s, 1 H) 6.83 (d, J=8.1 Hz, 1 H) 6.96 (t, J=7.1 Hz, 1 H) 7.23 (dd, J=7.6, 1.0 Hz, 1 H) 7.29 (m, 1 H) 7.41 (d, J=8.1 Hz, 1 H) 7.46 (dd, J=8.6, 2.0 Hz, 1 H) 7.72 (d, J=1.5 Hz, 1 H) 7.83 (s, 1 H. Mass spectrum m/z 355.24 (M+H)$^+$, 377.16 (M+Na)$^+$.

Examples 2-2 to 2-4

Examples 2-2 to 2-4 set forth in Table 1 below were prepared using the methods described in Example 2-1:

TABLE 1

| Example | Compound name | Mass spectrum |
|---|---|---|
| 2-2 | racemic 2-(4-chlorophenyl)-2H-chromene-3-carboxylic acid | 287.0 (M + H)$^+$ |
| 2-3 | racemic 2-(4-methoxyphenyl)-2H-chromene-3-carboxylic acid | 283.1 (M + H)$^+$ |
| 2-4 | racemic 2-(3,5-dichlorophenyl)-2H-chromene-3-carboxylic acid | 319.0 (M − H)$^-$ |

Example 3

Preparation of racemic 2-(benzo[d][1,3]dioxol-5-yl)-2H-chromene-3-carboxylic acid Step 1. A mixture of methyl 3-(2-hydroxyphenyl)-3-oxopropanoate (prepared according to Cushman, M. et al., *J. Med. Chem.* 1991, 34, 798; 200 mg, 1.03 mmol) and piperonal (155 mg, 1.03 mmol) in isopropanol (5.0 mL) was treated with piperidine (10 µL, 103 µmol) and acetic acid (5.9 µL, 103 µmol) and then heated at reflux for 15.5 h. At the conclusion of this period, the solution was treated with water (1.0 mL) and cooled to rt with stirring. Once at the prescribed temperature, the mixture was concentrated and purified by column chromatography (silica gel, 2-25% ethyl acetate/hexane) to provide a cloudy oil (172 mg). The cloudy oil was crystallized from methanol to provide methyl 2-(benzo[d][1,3]dioxol-5-yl)-4-oxochroman-3-carboxylate as a white solid (63 mg, 19%). The NMR indicated predominantly the enolic form. $^1$H NMR (400 MHz, CDCl$_3$) δ ppm 3.76 (s, 3 H) 5.91 (m, 2 H) 6.15 (s, 1 H) 6.70 (d, J=8.1 Hz, 1 H) 6.78 (d, J=8.1 Hz, 1 H) 6.82 (dd, J=8.1, 1.5 Hz, 1 H) 6.86 (d, J=2.0 Hz, 1 H) 6.96 (dt, J=7.6, 1.0 Hz, 1 H) 7.28 (m, 1 H) 7.68 (dd, J=7.6, 1.5 Hz, 1 H) 12.26 (br. s, 1 H). Mass spectrum m/z 349.18 (M+Na)$^+$.

Step 2. A solution of methyl 2-(benzo[d][1,3]dioxol-5-yl)-4-oxochroman-3-carboxylate (58 mg, 178 µmol) in tetrahydrofuran (1.0 mL) was diluted with methanol (2.0 mL) and stirred on an ice/acetone bath. Sodium borohydride (7 mg, 178 µmol) was added and the resulting mixture was stirred for 40 min. After this time, water (about 10 mL) was added and the mixture was stirred while warming to rt. The resulting white solid was collected by filtration, washed with water and dried under vacuum to provide racemic methyl 2-(benzo[d][1,3]dioxol-5-yl)-4-hydroxychroman-3-carboxylate (51 mg, 87%). $^1$H NMR (400 MHz, CDCl$_3$) δ ppm 2.69 (s, 1 H) 3.47 (dd, J=6.6, 2.5 Hz, 1 H) 3.51 (s, 3 H) 5.25 (d, J=5.6 Hz, 1 H) 5.31 (d, J=2.5 Hz, 1 H) 5.99 (s, 2 H) 6.82 (d, J=8.1 Hz, 1 H) 6.89 (d, J=8.1 Hz, 1 H) 6.92 (m, 2 H) 7.03 (t, J=7.4 Hz, 1 H) 7.23 (td, J=7.1, 1.0 Hz, 1 H) 7.57 (d, J=7.6 Hz, 1 H). Mass spectrum m/z 351.20 (M+Na)$^+$.

Step 3. A suspension of racemic methyl 2-(benzo[d][1,3]dioxol-5-yl)-4-hydroxychroman-3-carboxylate (49 mg, 149 µmol) in dichloromethane (2.0 mL) was stirred on an ice bath and treated with triethylamine (31 µL, 224 µmol), then dropwise with methanesulfonyl chloride (13 µL, 164 µmol). The cooling bath was removed after 90 min and the solution was stirred at rt for 23 h. At the conclusion of this period, the solution was diluted with additional dichloromethane, washed with 1.0 M aqueous HCl, dried over sodium sulfate and concentrated under vacuum to yield a residue. The residue was dissolved in benzene (2.0 mL), treated with 1,8-diazabicyclo[5.4.0]undec-7-ene (30 µL, 224 µmol) and stirred at 60° C. for 3.75 h. After this time, the mixture was cooled to rt and then diluted with ethyl acetate, washed with 1.0 M aqueous HCl, water, and saturated aqueous sodium chloride, dried over sodium sulfate and concentrated under vacuum. The resulting residue was purified by column chromatography (silica gel, 2-10% ethyl acetate/hexane) to provide racemic methyl 2-(benzo[d][1,3]dioxol-5-yl)-2H-chromene-3-carboxylate as a white solid (27 mg, 58%). $^1$H NMR (400 MHz, CDCl$_3$) δ ppm 3.77 (s, 3 H) 5.91 (m, 2 H) 6.18 (s, 1 H) 6.71 (d, J=8.6 Hz, 1 H) 6.78 (d, J=8.1 Hz, 1 H) 6.85 (m, 2 H) 6.90 (t, J=7.4 Hz, 1 H) 7.19 (m, 2 H) 7.67 (s, 1 H).

Step 4. A solution of racemic methyl 2-(benzo[d][1,3]dioxol-5-yl)-2H-chromene-3-carboxylate (26 mg, 84 µmol) in tetrahydrofuran (1.0 mL) was treated with 1.0 M aqueous sodium hydroxide (1.0 mL) and the mixture was stirred vigorously at rt for 23.5 h. After this time, the THF was removed under a nitrogen stream, and the resulting aqueous residue was acidified with 1.0 M aqueous HCl. The resulting solid was collected by filtration, washed with water and dried under vacuum to provide Example 3 as a white powder (19 mg, 77%). $^1$H NMR (400 MHz, CDCl$_3$) δ ppm 5.91 (m, 2 H) 6.16 (s, 1 H) 6.71 (d, J=8.6 Hz, 1 H) 6.79 (d, J=8.1 Hz, 1 H) 6.86 (m, 2 H) 6.91 (t, J=7.4 Hz, 1 H) 7.21 (m, 2 H) 7.76 (s, 1 H). Mass spectrum m/z 297.29 (M+H)$^+$.

Example 4-1

Preparation of racemic 2-(3,4-dichlorophenyl)-2-methyl-2H-chromene-3-carboxylic acid Step 1. In a dried flask, a solution of methyl acetoacetate (2.16 mL, 20.0 mmol) in toluene (100 mL) was treated with sodium hydride (60% mineral oil dispersion, 880 mg, 22.0 mmol). The resulting mixture was stirred at rt for 10 min, and then a solution of 2-fluorobenzoyl chloride (2.23 mL, 20.0 mmol) in toluene (50 mL) was added over about a 1 min. period. The resulting mixture was heated at reflux for 24.5 h, and then poured into water (200 mL). The mixture was extracted twice with ether (50 mL each). The combined organic phases were dried over sodium sulfate and concentrated under vacuum to provide a viscous yellow oil, which crystallized. The solid was recrystallized from a ethyl acetate/hexane solution to provide methyl 2-methyl-4-oxo-4H-chromene-3-carboxylate as off-white crystals in two crops (2.10 g, 48%). $^1$H NMR (400 MHz, CDCl$_3$) δ ppm 2.53 (s, 3 H) 3.94 (s, 3 H) 7.42 (m, 2 H) 7.67 (ddd, J=8.5, 7.0, 1.8 Hz, 1 H) 8.21 (dd, J=7.9, 1.8 Hz, 1 H).

Step 2. A suspension of copper(I) chloride (454 mg, 4.58 mmol) in tetrahydrofuran (5.0 mL) was stirred in a dry flask under nitrogen on ice. A solution of (3,4-dichlorophenyl)magnesium bromide (0.5 M) in THF (9.17 mL, 4.58 mmol) was added over about a 2 min. period. The resulting mixture was stirred on ice for 5 min, and then treated with a solution of methyl 2-methyl-4-oxo-4H-chromene-3-carboxylate (500 mg, 2.29 mmol) in THF (6.0 mL) over about a 2 min. period. The mixture was stirred on ice for 10 min, and then allowed to warm to rt. After 4.5 h at rt, the reaction mixture was quenched by adding 9:1 saturated aqueous ammonium chloride/aqueous ammonia (20 mL). Upon completion of addition, the reaction mixture was stirred at rt for 10 min. and then ethyl acetate and additional ammonium chloride were added. The aqueous and organic layers were mixed well and then separated. The organic layer was washed twice with saturated ammonium chloride, dried over sodium sulfate and then concentrated under vacuum to yield a residue. The residue was purified by column chromatography (silica gel, 9:1 hexane-ethyl acetate) to provide methyl 2-(3,4-dichlorophenyl)-2-methyl-4-oxochroman-3-carboxylate as a colorless gum (518 mg, 62%). By NMR, this material was mixture of the enol form and 2 diastereomeric keto forms (ratio about 1:1:2). Mass spectrum m/z 387.01, 389.03 (M+Na)$^+$.

Step 3. A solution of methyl 2-(3,4-dichlorophenyl)-2-methyl-4-oxochroman-3-carboxylate (490 mg, 1.34 mmol) in THF (2.0 mL) was diluted with methanol (4.0 mL) and treated at rt with sodium borohydride (51 mg, 1.34 mmol). Additional sodium borohydride was added after 4 h. After 2.5 h more the solution was concentrated under vacuum. The residue was partitioned between water (containing a few drops of 1.0 M aqueous sodium hydroxide) and ethyl acetate. The organic phase was dried over sodium sulfate and concentrated under vacuum to provide crude methyl 2-(3,4-dichlorophenyl)-4-hydroxy-2-methylchroman-3-carboxylate as a white solid (485 mg, 98%), which was used without further purification. Mass spectrum m/z 389, 391 (M+Na)$^+$.

Step 4. A solution of crude methyl 2-(3,4-dichlorophenyl)-4-hydroxy-2-methylchroman-3-carboxylate (100 mg, 272 µmol) in dichloromethane (2.0 mL) was stirred on an ice bath and treated with triethylamine (76 µL, 545 µmol), then dropwise with methanesulfonyl chloride (23 µL, 300 µmol). After stirring for 1.5 h, the solution was warmed to rt. After stirring at rt for 6 h, the solution was diluted with dichloromethane, washed with 1.0 M aqueous HCl, dried over sodium sulfate and concentrated under vacuum. The resulting residue was dissolved in benzene (2.0 mL), treated with 1,8-diazabicyclo[5.4.0]undec-7-ene (55 µL, 408 µmol) and stirred at rt for 25 min. After this time, the resulting mixture was heated to 60° C. where it stirred for 5.25 h. After this time, the solution was cooled to rt, diluted with ethyl acetate, washed with water, 1.0 M aqueous HCl, saturated aqueous sodium bicarbonate and saturated aqueous sodium chloride, dried over sodium sulfate and then concentrated under vacuum to yield a residue. The residue was purified by rotary TLC (silica gel, 92:8 hexane-ethyl acetate) to provide racemic methyl 2-(3,4-dichlorophenyl)-2-methyl-2H-chromene-3-carboxylate as a colorless gum (44 mg, 46%). $^1$H NMR (400 MHz, CDCl$_3$) δ ppm 2.02 (s, 3 H) 3.73 (s, 3 H) 6.82 (d, J=8.1 Hz, 1 H) 6.92 (dt, J=7.6, 1.0 Hz, 1 H) 7.15 (dd, J=7.6, 1.5 Hz, 1 H) 7.25 (dt, J=7.9, 1.5 Hz, 1 H) 7.37 (m, 2 H) 7.58 (s, 1 H) 7.61 (t, J=1.5 Hz, 1 H).

Step 5. A solution of racemic methyl 2-(3,4-dichlorophenyl)-2-methyl-2H-chromene-3-carboxylate (44 mg, 126 µmol) in methanol (1.0 mL) was treated with 1.0 M aqueous sodium hydroxide (1.0 mL) and heated at reflux for 4.25 h. After this time, the solution was cooled to rt, and then acidified with 1.0 M aqueous HCl, forming a dense white precipitate. The reaction mixture was diluted with water (2 mL) and the resulting solid was collected by filtration, washed with water and dried to provide Example 4-1 as a white solid (33 mg, 78%). $^1$H NMR (400 MHz, CDCl$_3$) δ ppm 2.04 (s, 3 H) 6.83 (d, J=8.1 Hz, 1 H) 6.93 (dt, J=7.6, 1.0 Hz, 1 H) 7.17 (dd, J=7.6, 1.5 Hz, 1 H) 7.28 (m, 1 H) 7.37 (m, 2 H) 7.60 (s, 1 H) 7.74 (s, 1 H).

Example 4-2

Preparation of racemic 2-(3,4-dichlorophenyl)-2-ethyl-2H-chromene-3-carboxylic acid Using the procedures of Example 4-1, methyl 3-oxopentanoate was converted to Example 4-2 as a white solid (16%). $^1$H NMR (400 MHz, CDCl$_3$) δ ppm 1.07 (t, J=7.1 Hz, 3 H) 2.22 (dq, J=14.3, 7.4 Hz, 1 H) 2.68 (dq, J=14.3, 7.4 Hz, 1 H) 6.87 (d, J=8.1 Hz, 1 H) 6.90 (t, J=7.6 Hz, 1 H) 7.14 (dd, J=7.6, 1.5 Hz, 1 H) 7.28 (m, 1 H) 7.35 (m, 2 H) 7.59 (t, J=1.3 Hz, 1 H) 7.80 (s, 1 H). High resolution mass spectrum m/z 347.0247 (M−H)$^-$, calc. 347.0247.

Example 5-1

Preparation of racemic 2-(3,4-dichlorophenyl)-2H-chromene-3-carboxylic acid

Step 1. A mixture of methyl 3-(2-hydroxyphenyl)-3-oxopropanoate (prepared according to Cushman, M. et al., *J. Med. Chem.* 1991, 34, 798; 500 mg, 2.56 mmol) and 3,4-dichlorobenzaldehyde (496 mg, 2.83 mmol) in isopropanol (5.0 mL) was treated with piperidine (25 µl, 257 µmol) and acetic acid (15 µl, 257 µmol) and then heated to reflux for 20 h. At the conclusion of this period, the mixture was cooled on ice, causing a gum to separate from the solution. The mixture was treated with a small amount of water and heated until homogeneous. On slow cooling to rt, a solid formed, which was collected by filtration and dried under vacuum to provide racemic methyl 2-(3,4-dichlorophenyl)-4-oxochroman-3-carboxylate as an off-white powder (496 mg, 55%). An additional sample (57 mg, 6%) was obtained by partial concentration of the filtrate. The NMR indicated predominantly the enolic form. $^1$H NMR (400 MHz, CDCl$_3$) δ ppm 3.78 (s, 3 H) 6.18 (s, 1 H) 6.81 (dd, J=8.1, 1.0 Hz, 1H) 6.99 (td, J=7.4, 1.0 Hz, 1 H) 7.19 (dd, J=8.4, 1.8 Hz, 1 H) 7.31 (m, 1 H) 7.34 (d, J=8.1 Hz, 1 H) 7.43 (d, J=2.0 Hz, 1 H) 7.69 (dd, J=7.9, 1.8 Hz, 1 H) 12.28 (br. s, 1H). High resolution mass spectrum m/z found 373.0016, calcd 373.0010 (M+Na)$^+$.

Step 2a. A solution of racemic methyl 2-(3,4-dichlorophenyl)-4-oxochroman-3-carboxylate (100 mg, 285 µmol) in THF (2.0 mL) was diluted with methanol (4.0 mL) and stirred on an ice/acetone bath. Sodium borohydride (11 mg, 285 µmol) was added and the resulting mixture was stirred for 40 min. After this time, the mixture was diluted with water and stirred while warming to rt. The resulting white solid was collected by filtration, washed with water and dried under vacuum to provide methyl 2-(3,4-dichlorophenyl)-4-hydroxychroman-3-carboxylate (90 mg). $^1$H NMR (400 MHz, CDCl$_3$) δ ppm 3.49 (s, 3 H) 3.51 (m, 1 H) 5.26 (d, J=6.1 Hz, 1 H) 5.35 (d, J=2.5 Hz, 1 H) 6.94 (dd, J=8.1, 1.0 Hz, 1 H) 7.06 (td, J=7.6, 1.0 Hz, 1 H) 7.22-7.29 (m, 2 H) 7.47 (d, J=8.6 Hz, 1 H) 7.56 (d, J=1.5 Hz, 1 H) 7.58 (d, J=7.6 Hz, 1 H).

Step 2b. Methyl 2-(3,4-dichlorophenyl)-4-hydroxychroman-3-carboxylate (90 mg) and p-toluenesulfonic acid hydrate (24 mg, 128 µmol) were dissolved in toluene (4.0 mL) and heated to reflux. After 40 min, the solution was cooled to rt, diluted with ethyl acetate, washed with saturated aqueous sodium bicarbonate, dried over sodium sulfate and concentrated under vacuum to provide racemic methyl 2-(3,4-dichlorophenyl)-2H-chromene-3-carboxylate as a white solid (90 mg, 94%). $^1$H NMR (400 MHz, CDCl$_3$) δ ppm 3.79 (s, 3 H) 6.21 (s, 1 H) 6.81 (d, J=8.1 Hz, 1 H) 6.93 (t, J=7.6 Hz, 1 H) 7.17-7.25 (m, 3 H) 7.35 (d, J=8.6 Hz, 1 H) 7.44 (d, J=2.0 Hz, 1 H) 7.70 (s, 1 H).

Step 3. Racemic methyl 2-(3,4-dichlorophenyl)-2H-chromene-3-carboxylate (90 mg, 268 µmol) was suspended in methanol (1.5 mL) and then treated with 1.0 M aqueous sodium hydroxide (1.5 mL). The resulting suspension was heated to reflux. After 2 h at reflux, the solution was acidified with 1.0 M aqueous HCl (1.5 mL) and cooled to rt with stirring. The resulting solid was collected by filtration, washed with water and dried under vacuum to provide Example 5-1 as a pale yellowish solid (73 mg, 85%). $^1$H NMR (400 MHz, CDCl$_3$) δ ppm 6.20 (s, 1 H) 6.82 (d, J=8.1 Hz, 1 H) 6.95 (td, J=7.4, 1.0 Hz, 1 H) 7.20-7.29 (m, 3 H) 7.36 (d, J=8.1 Hz, 1 H) 7.45 (d, J=2.0 Hz, 1 H) 7.81 (s, 1 H). Mass spectrum m/z 321.24 (M+H)$^+$.

Example 5-2

Preparation of racemic 2-(4-chloronaphthalen-1-yl)-2H-chromene-3-carboxylic acid Step 1. Following the procedure of Step 1, Example 5-1, 4-chloro-1-naphthaldehyde (prepared according to the procedure reported in PCT Patent Application WO 02/17712, 196 mg, 1.03 mmol) was converted to racemic methyl 2-(4-chloronaphthalen-1-yl)-4-oxochroman-3-carboxylate (127 mg, 34%).

Step 2. Following the procedure of Step 2, Example 5-1, racemic methyl 2-(4-chloronaphthalen-1-yl)-4-oxochroman-3-carboxylate (124 mg, 338 µmol) was converted to racemic methyl 2-(4-chloronaphthalen-1-yl)-2H-chromene-3-carboxylate. In contrast to the procedure of Step 2, Example 5-1, the crude product was purified by column chromatography (silica gel, ethyl acetate-hexane, 2-10%) to provide a white glassy foam (98 mg, 83%). $^1$H NMR (400 MHz, CDCl$_3$) δ ppm 3.73 (s, 3 H) 6.88 (td, J=7.6, 1.0 Hz, 1 H) 7.06 (s, 1 H) 7.10 (td, J=7.8, 1.8 Hz, 1 H) 7.22-7.27 (m, 2 H) 7.38 (d, J=7.6 Hz, 1 H) 7.64-7.76 (m, 2 H) 7.90 (s, 1 H) 8.32 (dd, J=8.6, 1.0 Hz, 1 H) 8.62 (d, J=8.1 Hz, 1 H).

Step 3. Following the procedure of Step 3, Example 5-1, racemic methyl 2-(4-chloronaphthalen-1-yl)-2H-chromene-3-carboxylate (98 mg, 279 µmol) was converted to Example 5-2, isolated as a white powder (85 mg, 90%). $^1$H NMR (400 MHz, CDCl$_3$) δ ppm 6.58 (d, J=8.1 Hz, 1 H) 6.93 (t, J=7.4 Hz, 1 H) 7.06 (s, 1 H) 7.14 (t, J=7.6 Hz, 1 H) 7.28 (d, J=7.6 Hz, 1 H) 7.46 (d, J=7.6 Hz, 1 H) 7.61 (d, J=8.1 Hz, 1 H) 7.80 (t, J=8.1 Hz, 1 H) 7.84 (t, J=7.1 Hz, 1 H) 7.96 (s, 1 H) 8.27 (d, J=8.1 Hz, 1 H) 8.69 (d, J=8.1 Hz, 1 H) 12.95 (s, 1 H). High resolution mass spectrum m/z 695.0984 (2M+Na)$^+$, calc. 695.0999.

Example 5-3

Preparation of racemic 2-(pyridin-4-yl)-2H-chromene-3-carboxylic acid trifluoroacetic acid salt Step 1. Following the procedure of Step 1, Example 5-1, picolinaldehyde (120 µl, 1.29 mmol) was converted to racemic methyl 2-(pyridin-4-yl)-4-oxochroman-3-carboxylate. In contrast to Step 1, Example 5-1, the product failed to crystallize from the reaction mixture, which was concentrated and the resulting residue was purified by column chromatography (silica gel, 1-100% ethyl acetate-hexane) to provide an oil (100 mg, 27%). By NMR, this oil was a mixture of the enol and keto forms (ratio about 6:4). $^1$H NMR (400 MHz, CDCl$_3$) δ ppm 3.70 (s, keto 3H) 3.82 (s, enol 3 H) 4.01 (d, J=11.7 Hz, keto 1 H) 5.74 (d, J=11.7 Hz, keto 1 H) 6.23 (s, enol 1 H) 6.88 (d, J=8.1 Hz, enol 1 H) 6.99 (t, J=7.9 Hz, enol 1 H) 7.07 (d, J=8.1 Hz, keto 1 H) 7.12 (t, J=8.1 Hz, keto 1 H) 7.26 (d, J=6.1 Hz, enol 2 H) 7.32 (t, enol 1 H) 7.41 (d, J=6.1 Hz, keto 2 H) 7.58 (t, J=8.6 Hz, keto 1 H) 7.68 (dd, J=7.6, 1.5 Hz, enol 1 H) 7.95 (dd, J=7.9, 1.8 Hz, keto 1 H) 8.52 (d, J=6.1 Hz, enol 2 H) 8.68 (d, J=6.1 Hz, keto 2 H) 12.25 (br. s, enol 1 H). Mass spectrum m/z 284.2 (M+H)$^+$.

Step 2. A solution of racemic methyl 2-(pyridin-4-yl)-4-oxochroman-3-carboxylate (100 mg, 353 µmol) in methanol (5.0 mL) was stirred on an ice/acetone bath. Sodium borohydride (27 mg, 707 µmol) was added and the mixture was stirred for 2 h while warming to rt. Once at the prescribed temperature, the mixture was diluted with saturated aqueous sodium bicarbonate and extracted three times with ethyl acetate. The combined organic phases were dried over sodium sulfate and concentrated under vacuum. The resulting residue was dissolved in toluene (5.0 mL), treated with p-toluenesulfonic acid hydrate (135 mg, 709 µmol). The resulting mixture was heated at reflux for 2 h. After this time, the mixture was cooled to rt, diluted with water and ethyl acetate, and then treated with 1.0 M aqueous sodium hydroxide (5.0 mL). The aqueous and organic layers were separated and the aqueous phase was extracted twice more with ethyl acetate. The combined organic phases were dried over sodium sulfate and concentrated under vacuum to yield a residue. The residue (100 mg) was used without further purification. Mass spectrum m/z 268.2 (M+H)$^+$.

Step 3. Following the procedure of Step 3, Example 5-1, crude racemic methyl 2-(pyridin-4-yl)-2H-chromene-3-carboxylate (100 mg, 375 µmol) was converted to racemic 2-(pyridin-4-yl)-2H-chromene-3-carboxylic acid. In contrast to Step 3, Example 5-1, the product was purified by preparative HPLC [(C$_{18}$, 5-95% acetonitrile-water (containing 0.05% trifluoroacetic acid)] and lyophilization to provide Example 5-3 as a yellow solid (30 mg, 22%). $^1$H NMR (400 MHz, CDCl$_3$) δ ppm 6.47 (s, 1 H) 7.00 (d, J=8.1 Hz, 1 H) 7.03 (t, J=7.6 Hz, 1 H) 7.24 (dd, J=7.4, 1.3 Hz, 1 H) 7.37 (t, J=7.1 Hz, 1 H) 7.78 (s, 1 H) 7.94 (d, J=6.1 Hz, 2 H) 8.85 (d, J=6.6 Hz, 2 H). High resolution mass spectrum m/z 254.0817 (M+H)$^+$, calc. 254.0817.

Examples 5-4 to 5-26

Examples 5-4 to 5-26 set forth in Table 2 below were prepared using the methods described in Examples 5-1, 5-2 and 5-3:

TABLE 2

| Example | Compound name | Mass spectrum |
|---|---|---|
| 5-4 | racemic 2-(naphthalen-2-yl)-2H-chromene-3-carboxylic acid | 325.2 (M + Na)$^+$ |
| 5-5 | racemic 2-(naphthalen-1-yl)-2H-chromene-3-carboxylic acid | 301.2 (M − H)$^-$ |
| 5-6 | racemic 2-(3-fluorophenyl)-2H-chromene-3-carboxylic acid | 293.2 (M + Na)$^+$ |
| 5-7 | racemic 2-(3-fluoro-4-chlorophenyl)-2H-chromene-3-carboxylic acid | 305.3 (M + H)$^+$ |
| 5-8 | racemic 2-(3-chloro-4-fluorophenyl)-2H-chromene-3-carboxylic acid | 305.3 (M + H)$^+$ |
| 5-9 | racemic 2-(3-trifluoromethylphenyl)-2H-chromene-3-carboxylic acid | 321.3 (M + H)$^+$ |
| 5-10 | racemic 2-(4-trifluoromethylphenyl)-2H-chromene-3-carboxylic acid | 319.1 (M − H)$^-$ |
| 5-11 | racemic 2-(3,4-difluorophenyl)-2H-chromene-3-carboxylic acid | 287.1 (M − H)$^-$ |
| 5-12 | racemic 2-(3-nitrophenyl)-2H-chromene-3-carboxylic acid | 296.1 (M − H)$^-$ |
| 5-13 | racemic 2-(3-nitro-4-chlorophenyl)-2H-chromene-3-carboxylic acid | 354.2 (M + Na)$^+$ |
| 5-14 | racemic 2-(3-methyl-4-chlorophenyl)-2H-chromene-3-carboxylic acid | 299.0 (M − H)$^-$ |
| 5-15 | racemic 2-(4-bromophenyl)-2H-chromene-3-carboxylic acid | 329.0 (M − H)$^-$ |
| 5-16 | racemic 2-(3-bromophenyl)-2H-chromene-3-carboxylic acid | 329.0 (M − H)$^-$ |
| 5-17 | racemic 2-(3,4-dibromophenyl)-2H-chromene-3-carboxylic acid | 406.9 (M − H)$^-$ |
| 5-18 | racemic 2-(3-fluoro-4-trifluoromethylphenyl)-2H-chromene-3-carboxylic acid | 337.0 (M − H)$^-$ |
| 5-19 | racemic 2-(4-methylphenyl)-2H-chromene-3-carboxylic acid | 265.1 (M − H)$^-$ |
| 5-20 | racemic 2-(3-methylphenyl)-2H-chromene-3-carboxylic acid | 265.1 (M − H)$^-$ |
| 5-21 | racemic 2-(pyridin-2-yl)-2H-chromene-3-carboxylic acid | 254.2 (M + H)$^+$ |
| 5-22 | racemic 2-(quinolin-2-yl)-2H-chromene-3-carboxylic acid | 304.2 (M + H)$^+$ |
| 5-23 | racemic 2-(quinolin-3-yl)-2H-chromene-3-carboxylic acid | 304.2 (M + H)$^+$ |
| 5-24 | racemic 2-(3-trifluoromethyl-4-fluoro-phenyl)-2H-chromene-3-carboxylic acid | 337.0 (M − H)$^-$ |
| 5-25 | racemic 2-(6-trifluoromethyl-pyridin-2-yl)-2H-chromene-3-carboxylic acid | 322.3 (M + H)$^+$ |
| 5-26 | racemic 2-(2,3-dichlorophenyl)-2H-chromene-3-carboxylic acid | 319.2 (M − H)$^-$ |

Examples 6a and 6b

Preparation of (−)-2-(3,4-dichlorophenyl)-2H-chromene-3-carboxylic acid and (+)-2-(3,4-dichlorophenyl)-2H-chromene-3-carboxylic acid, Respectively A sample of Example 5-26 (31 mg) was resolved using supercritical fluid chromatography (Chiralcel OJ, carbon dioxide-methanol 70-30, 100 bar, 35° C). The (−) isomer eluted first and was obtained in >99% enantiomeric purity (14 mg). $[\alpha]_D=-168.2°$ (MeOH, c=2.5 mg/mL). The (+) isomer eluted second and was obtained in >98% enantiomeric purity (14 mg). $[\alpha]_D=+176.8°$ (MeOH, c=2.5 mg/mL). NMR spectra of both isomers were identical to that of the racemic material.

Example 7-1

Preparation of racemic 2-(3-methoxy-4-chlorophenyl)-2H-chromene-3-carboxylic acid Step 1. A solution of 4-chloro-3-methoxybenzoic acid (1.12 g, 5.98 mmol) in THF (30 mL) was stirred on an ice bath and treated with a 1.0 M tetrahydrofuran solution of lithium aluminum hydride (7.18 mL, 7.18 mmol) over about a 5 min. period. The solution was stirred on ice for 2 h, and then quenched with rapid stirring by the slow dropwise addition of water (0.27 mL), followed by 15% aqueous sodium hydroxide (0.27 mL), then water (0.82 mL) again. Upon completion of addition, the resulting suspension was filtered and the collected solid was washed with ethyl acetate. The filtrate was concentrated under vacuum to provide (4-chloro-3-methoxyphenyl)methanol as a colorless oil (737 mg, 71%). $^1$H NMR (400 MHz, CDCl$_3$) δ ppm 3.92 (s, 3 H) 4.67 (s, 2 H) 6.87 (d, J=7.6 Hz, 1 H) 6.98 (s, 1 H) 7.33 (d, J=7.6 Hz, 1 H).

Step 2. A suspension of pyridinium chlorochromate (1.37 g, 6.34 mmol) in dichloromethane (35 mL) was treated with Celite (2.0 g) and stirred at rt. A solution of (4-chloro-3-methoxyphenyl)methanol (730 mg, 4.23 mmol) in dichloromethane (5 mL) was added in one portion, and the resulting mixture was stirred at rt for 3 h. After this time, the mixture was diluted with diethyl ether, and stirred vigorously. The mixture was then filtered through a pad of silica gel and the collected solids were rinsed with additional diethyl ether. The combined filtrates were concentrated under vacuum to provide 4-chloro-3-methoxybenzaldehyde as a pale tan-yellow solid (630 mg, 87%). $^1$H NMR (400 MHz, CDCl$_3$) δ ppm 3.98 (s, 3 H) 7.41 (dd, J=7.9, 1.8 Hz, 1 H) 7.45 (d, J=2.0 Hz, 1 H) 7.55 (d, J=7.6 Hz, 1 H) 9.95 (s, 1 H).

Step 3. Following the procedure described in Step 1, Example 5-1, 4-chloro-3-methoxybenzaldehyde (132 mg, 772 μmol) was converted to racemic methyl 2-(3-methoxy-4-chlorophenyl)-4-oxochroman-3-carboxylate. In contrast to the procedure described in Step 1, Example 5-1, the crude product was not a solid, and rather was purified by column chromatography (silica gel, 5-20% ethyl acetate-hexane) to provide a colorless gum (172 mg, 64%). By NMR, this material was a mixture of the enol and keto forms (ratio about 7:3).

Step 4. Following the procedures described in Steps 2 and 3 of Example 5-1, racemic methyl 2-(3-methoxy-4-chlorophenyl)-4-oxochroman-3-carboxylate (169 mg, 487 μmol) was converted to Example 7-1 as a white solid (72 mg, 47%). $^1$H NMR (400 MHz, CDCl$^3$) δ ppm 3.80 (s, 3 H) 6.22 (s, 1 H) 6.79-6.86 (m, 2 H) 6.95 (t, J=7.4 Hz, 1 H) 7.19 (d, J=1.5 Hz, 1 H) 7.25 (td, J=7.6, 1.5 Hz, 1 H) 7.35 (d, J=8.1 Hz, 1 H) 7.40 (dd, J=7.4, 1.3 Hz, 1 H) 7.74 (s, 1 H) 12.98 (s, 1 H). High resolution mass spectrum m/z 315.0430 (M−H)$^-$, calc. 315.0424.

Examples 7-2 to 7-5

Examples 7-2 to 7-5 set forth in Table 3 below were prepared using the methods described in Example 7-1:

TABLE 3

| Example | Compound name | Mass spectrum |
|---|---|---|
| 7-2 | racemic 2-(6-chloropyridin-3-yl)-2H-chromene-3-carboxylic acid | 288.2 (M + H)$^+$ |
| 7-3 | racemic 2-(5,6-dichloropyridin-3-yl)-2H-chromene-3-carboxylic acid | 322.0 (M + H)$^+$ |
| 7-4 | racemic 2-(3-bromo-4-chlorophenyl)-2H-chromene-3-carboxylic acid | 362.9 (M − H)$^-$ |
| 7-5 | racemic 2-(3-chloro-4-trifluoromethyl-phenyl)-2H-chromene-3-carboxylic acid | 353.0 (M − H)$^-$ |

Example 8

Preparation of racemic 2-(3,4-dichlorophenyl)-6-methoxy-2H-chromene-3-carboxylic acid Step 1. A solution of lithium bis(trimethylsilyl)amide (1.0 M in tetrahydrofuran, 61.5 mL, 61.5 mmol) was stirred at −78° C. and treated over a 5 min period with a solution of tert-butyl acetate (5.2 mL, 38.4 mmol) in tetrahydrofuran (13 mL). The resulting mixture was stirred at −78° C. for 55 min, and then treated dropwise with a solution of methyl 2-hydroxy-5-methoxybenzoate (1.63 mL, 10.98 mmol) in tetrahydrofuran (13 mL) over a 5 min period. The resulting solution was warmed slowly to rt where it stirred for 3 days. At the conclusion of this period, the solution was treated with ice-cold saturated aqueous ammonium chloride, and then extracted three times with ethyl acetate. The combined organic phases were dried over sodium sulfate and concentrated under vacuum to provide an oil. The oil was purified by column chromatography (silica gel, 20-30% ethyl acetate-hexane), and the effluent was concentrated to yield a residue. The residue was recrystallized from hexane to provide tert-butyl 3-(2-hydroxy-5-methoxyphenyl)-3-oxopropanoate as yellow crystals (2.40 g, 82%). $^1$H NMR (400 MHz, CDCl$_3$) δ ppm 1.46 (s, 9 H) 3.79 (s, 3 H) 3.89 (s, 2 H) 6.95 (d, J=9.2 Hz, 1 H) 7.11 (d, J=3.1 Hz, 1 H) 7.14 (dd, J=8.6, 2.5 Hz, 1 H) 11.54 (s, 1 H). Mass spectrum m/z 289.19 (M+Na)$^+$.

Step 2. A solution of tert-butyl 3-(2-hydroxy-5-methoxyphenyl)-3-oxopropanoate (500 mg, 1.88 mmol) in isopropanol (5.0 mL) was treated with 3,4-dichlorobenzaldehyde (329 mg, 1.88 mmol), piperidine (20 μL, 188 μmol) and acetic acid (10 μL, 188 μmol). The reaction mixture was heated at reflux overnight, and then treated with water (1.0 mL). The resulting mixture was cooled to rt and then concentrated under vacuum to yield a residue. The residue was purified by column chromatography (silica gel, 2-25% ethyl acetate-hexane) to provide racemic tert-butyl 2-(3,4-dichlorophenyl)-6-methoxy-4-oxochroman-3-carboxylate as a yellow oil (380 mg, 48%). This material was used without further purification in Step 3 below.

Step 3. A solution of racemic tert-butyl 2-(3,4-dichlorophenyl)-6-methoxy-4-oxochroman-3-carboxylate (100 mg, 236 μmol) in tetrahydrofuran (1.0 mL) was diluted with methanol (1.0 mL) and stirred at 0° C. Sodium borohydride (12 mg, 473 μmol) was added and the resulting mixture was stirred for 30 min. After this time, water (2.0 mL) was added and the mixture was stirred at rt. The resulting white solid was collected by filtration and dried under vacuum, and then purified by column chromatography (silica gel, 5-55% ethyl acetate-hexane) to provide a diastereomeric mixture of tert-butyl 2-(3,4-dichlorophenyl)-4-hydroxy-6-methoxychroman-3-carboxylate (21 mg, 21%). This material was used without further purification in Step 4 below.

Step 4. A mixture of tert-butyl 2-(3,4-dichlorophenyl)-4-hydroxy-6-methoxychroman-3-carboxylate (21 mg, 49 μmol) and p-toluenesulfonic acid hydrate (5 mg, 25 μmol) in toluene (5 mL) was heated at reflux for 30 min. At the conclusion of this period, the solution was cooled to rt and then concentrated under vacuum to yield a residue. The residue was treated with water and the resulting solid was collected by filtration and then dried under vacuum. The resulting material was purified by column chromatography (silica gel, 0-50% ethyl acetate-hexane) and then again by rotary thin-layer chromatography (silica gel, hexane-ethyl acetate) to provide Example 8 (5 mg, 28%). $^1$H NMR (400 MHz, CDCl$_3$) δ ppm 3.77 (s, 3 H) 6.16 (s, 1 H) 6.74-6.78 (m, 2 H) 6.83 (dd, J=9.2, 3.1 Hz, 1 H) 7.21 (dd, J=8.6, 2.0 Hz, 1 H) 7.35 (d, J=8.1 Hz, 1 H) 7.44 (d, J=2.0 Hz, 1 H) 7.76 (s, 1 H). Mass spectrum m/z 349.2 (M–H)$^-$.

Example 9-1

Preparation of racemic 2-(3,4-dichlorophenyl)-7-fluoro-2H-chromene-3-carboxylic acid Step 1. A 1.0 M tetrahydrofuran solution of lithium bis(trimethylsilyl)amide (39.0 mL, 39.0 mmol) was stirred at –78° C. and treated over a 25 min period with a solution of 1-(4-fluoro-2-hydroxyphenyl)ethanone (2.00 g, 13.0 mmol) in 50 mL of tetrahydrofuran. The resulting solution was stirred at –78° C. for 1 h, and then at –15° C. for 2 h. After being cooled again to –78° C., the solution was treated with a solution of dimethyl carbonate (1.20 mL, 14.3 mmol) in tetrahydrofuran (5 mL). The resulting mixture was allowed to warm to rt where it stirred overnight. After this time, the mixture was poured over ice and then concentrated hydrochloric acid (10 mL) was added. The resulting mixture was extracted three times with dichloromethane. The combined organic phases were washed twice with water, dried over sodium sulfate and then concentrated under vacuum to yield a residue. The residue was purified by radial thin-layer chromatography (silica gel, 2-40% ethyl acetate-hexane) to provide methyl 3-(4-fluoro-2-hydroxyphenyl)-3-oxopropanoate as a white solid (1.76 g, 64%). $^1$H NMR (400 MHz, CDCl$_3$) δ ppm 3.78 (s, 3 H) 3.98 (s, 2 H) 6.62-6.71 (m, 2 H) 7.69 (dd, J=8.9, 6.4 Hz, 1 H) 12.15 (d, J=1.5 Hz, 1 H). Mass spectrum m/z 213.14 (M+H)$^+$.

Step 2. Following the procedure described in Step 1, Example 5-1, methyl 3-(4-fluoro-2-hydroxyphenyl)-3-oxopropanoate (500 mg, 2.36 mmol) was converted to racemic methyl 2-(3,4-dichlorophenyl)-7-fluoro-4-oxochroman-3-carboxylate. In contrast to the procedure described in Step 1, Example 5-1, the crude product was purified by column chromatography (silica gel, ethyl acetate-hexane) to provide a white solid (630 mg, 72%). By NMR this material was a mixture of the enol and keto forms (ratio about 7:3).

Step 3. Following the procedures described in Steps 2 and 3, Example 5-1, racemic methyl methyl 2-(3,4-dichlorophenyl)-7-fluoro-4-oxochroman-3-carboxylate (100 mg, 271 μmol) was converted to Example 9-1 as a pale yellow solid (37 mg, 40%). $^1$H NMR (400 MHz, CDCl$_3$) δ ppm 6.20 (s, 1 H) 6.56 (dd, J=9.7, 2.0 Hz, 1 H) 6.67 (td, J=8.4, 2.5 Hz, 1 H) 7.19-7.23 (m, 2 H) 7.38 (d, J=8.1 Hz, 1 H) 7.44 (d, J=2.0 Hz, 1 H) 7.77 (s, 1 H). Mass spectrum m/z 337.2 (M–H)$^-$.

Examples 9-2 to 9-6

Examples 9-2 to 9-6 set forth in Table 4 below were prepared using the methods described in Example 9-1:

TABLE 4

| Example | Compound name | Mass spectrum |
|---------|---------------|---------------|
| 9-2 | racemic 2-(3,4-dichlorophenyl)-6-chloro-2H-chromene-3-carboxylic acid | 353.0 (M – H)$^-$ |
| 9-3 | racemic 2-(3,4-dichlorophenyl)-2H-benzo[h]chromene-3-carboxylic acid | 369.1 (M – H)$^-$ |
| 9-4 | racemic 2-(3,4-dichlorophenyl)-6-fluoro-2H-chromene-3-carboxylic acid | 337.1 (M – H)$^-$ |
| 9-5 | racemic 2-(3,4-dichlorophenyl)-7-bromo-2H-chromene-3-carboxylic acid | 396.9 (M – H)$^-$ |
| 9-6 | racemic 2-(3,4-dichlorophenyl)-7-methoxy-2H-chromene-3-carboxylic acid | 349.1 (M – H)$^-$ |

Utility

In general, compounds of the present invention, such as particular compounds disclosed in the preceding examples, have been shown to be modulators of chemokine receptor activity (for example, by displaying Ki values <10,000 nM in a binding assay such as those set forth below). By displaying activity as modulators of chemokine receptor activity, compounds of the present invention are expected to be useful in the treatment of human diseases associated with chemokines and their cognate receptors.

Antagonism of MCP-1 Binding to Human PBMC
(Yoshimura et al., *J. Immunol.* 1990, 145, 292)

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 μM radioligand) and 50 μl of binding buffer containing 5×10$^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx
(Sullivan et al., *Methods Mol. Biol.* 1999, 114, 125-133)

Calcium mobilization is measured using the fluorescent Ca$^{2+}$ indicator dye, Fluo-3. Cells are incubated at 8×10$^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., *J. Immunol. Methods* 1990, 36, 89-97 or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of 2-4×$10^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 ρl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

THP-1 Monocytic Cell Binding: Whole Cell-Based Assay

The human CCR2 binding assay was also established with the THP-1 human monocytic leukemic cell line, which expresses endogenous CCR2, using $^{125}$I-human MCP-1 as the tracer ligand. Radioligand competition binding assays were used for assessment of binding affinity of test compounds to the CCR2 receptor. For radioligand competition studies, 100 μl containing 2.5×$10^5$ THP-1 cells/well (in assay buffer containing 50 mM HEPES, pH7.4, 5mM $MgCl_2$, 1 mM $CaCl_2$ and 0.5% BSA) were added to 96-well assay plates containing the test compounds in 3-fold serial dilution, with final concentrations ranging from 5 μM to 100 μM. Subsequently, 50 μl $^{125}$I-MCP-1 radioligand at a final concentration of 0.2 nM in assay buffer were added to the reaction. After a 90 minute incubation period at room temperature, the binding reaction was terminated by harvesting on GF/B filter plates (PerkinElmer Cat. No. 6005177) followed by washing with ice-cold wash buffer (50 mM HEPES, pH 7.4, 0.1% BSA, 0.5 M NaCl) to remove unbound ligand. After washing, the plate was dried for 45 minutes at 60° C. followed by addition of 40 μl MicroScint 20 scintillation fluid, sealed and analyzed by the Packard TopCount reader. Non-specific binding was determined in the presence of 10 μM (a molar excess of 5000 fold) of an in-house CCR2 small molecule antagonist (CCR2 IC50=2 nM). Specific binding of $^{125}$I-MCP-1 was calculated as the difference between total and non-specific binding. The competition data was plotted as a percentage inhibition of radioligand specific bound in the absence of test compound (percent of total signal). After correcting for non-specific binding, IC50 values were determined The IC50 is defined as the concentration of test compound required to reduce $^{125}$I-MCP-1 specific binding by 50% and was calculated using the four parameter logistic equation to fit the normalized data.

Antagonism of MCP-1-Induced Human PBMC Chemotaxis (Bacon et al., *Brit. J. Pharmacol.* 1988, 95, 966)

Neuroprobe MBA96-96-well chemotaxis chamber, Polyfiltronics MPC 96 well plate, and Neuroprobe polyvinylpyrrolidone-free polycarbonate PFDS 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at 1×$10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell Derivation and Cell Culture

A pool of HT1080 cells stably expressing endogenous CC chemokine receptor 5 (CCR5) were developed using the methods outlined by Harrington, Sherf, and Rundlett (see U.S. Pat. Nos. 6,361,972 and 6,410,266). The highest-expressing clones were isolated using repetitive flow cytometry, followed by sub-cloning. These cells were then cultured in 6-well dishes at $3 \times 10^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation

A cell pellet containing $1 \times 10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding Assay

The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of [$^{125}$I]-MIP-1 beta (Perkin Elmer; material was diluted in Binding buffer such that the addition of 50 microliters/well gives a final concentration of 0.1 nM [$^{125}$I]-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-Based Functional Assay

HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e., agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

At least one compound of the disclosure is an inhibitor of both CCR2 and CCR5 and may be used to treat diseases associated with either chemokine. These compounds of the present invention are considered dual antagonists.

Compounds of the present invention were tested in one of the assays described above and the results shown in Table 5 below were obtained.

TABLE 5

| Example | CCR2 Binding Ki, nM (n = 1 unless otherwise noted) |
|---|---|
| 1 | 2000 |
| 2-1 | 75 |
| 2-2 | 950 |
| 2-3 | 5300 |
| 2-4 | 4500 |
| 3 | 1100 |
| 4-1 | 220 |
| 4-2 | 1200 |
| 5-1 | 140 |
| 5-2 | 1900 |
| 5-3 | 1800 |
| 5-4 | 1800 |
| 5-5 | 1700 |
| 5-6 | 5700 |
| 5-7 | 290 |
| 5-8 | 560 |
| 5-9 | 1600 |
| 5-10 | 920 |
| 5-11 | 8600 |
| 5-12 | 2800 |
| 5-13 | 230 |
| 5-14 | 160 |
| 5-15 | 430 |
| 5-16 | 1700 |
| 5-17 | 85 |
| 5-18 | 720 |
| 5-19 | 4500 |
| 5-20 | 4200 |
| 5-21 | 1400 |
| 5-22 | 2100 |
| 5-23 | 4300 |
| 5-24 | 1100 |
| 5-25 | 8300 |

TABLE 5-continued

| Example | CCR2 Binding Ki, nM (n = 1 unless otherwise noted) |
|---|---|
| 5-26 | 2600 |
| 6a | 80 |
| 6b | 1700 |
| 7-1 | 2900 |
| 7-2 | 4500 |
| 7-3 | 570 |
| 7-4 | 170 |
| 7-5 | 390 |
| 8 | 360 |
| 9-1 | 350 |
| 9-2 | 300 |
| 9-3 | 1200 |
| 9-4 | 340 |
| 9-5 | 720 |
| 9-6 | 300 |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (Ancylostona braziliense, Ancylostoma caninum). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences* (Mack Publishing Company), a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of formula (I):

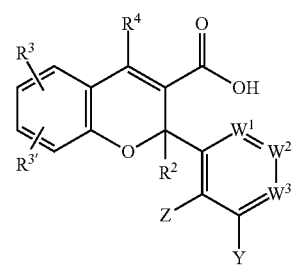

or a stereoisomer or a pharmaceutically acceptable salt thereof, wherein:

47

R² is H, or C₁₋₄ alkyl;
R³ and R³' are independently H, C₁₋₄ alkyl, C₁₋₄ alkoxy, halo, or haloC₁₋₄ alkyl;
or R³ and R³', when attached to neighboring carbons, taken together form —CH=CH—CH=CH—;
R⁴ is H or C₁₋₄ alkyl;
W¹ is C—Z';
W² is C—Y';
W³ is C—X;
X is H, C₁₋₄ alkyl, C₁₋₄ alkoxy, halo or haloC₁₋₄ alkyl;
Y' is H, C₁₋₄ alkyl, C₁₋₄ alkoxy, halo, haloC₁₋₄ alkyl or NO₂;
Y is H, C₁₋₄ alkyl, halo, halo-C₁₋₄-alkyl or NO₂;
Z and Z' are independently H or halo;
or Y and Z, Y' and Z', Y and X, or Y' and X are taken together to form —CH=CH—CH=CH—;
provided that:
(1) if W¹, W² and W³ are all CH, then Y cannot be H;
(2) if W¹, W² and W³ are all CH and Z is Cl, then Y is Cl; and
(3) if X is F then one of Y or Y' is not H.

2. The compound of claim 1, wherein:
R² is H, or C₁₋₄ alkyl;
R³ and R³' are independently H, C₁₋₄ alkyl, C₁₋₄ alkoxy, halo, or haloC₁₋₄ alkyl;
R⁴ is H or C₁₋₄ alkyl;
W¹ is C—Z';
W² is C—Y';
W³ is C—X;
X is H, C₁₋₄ alkyl, C₁₋₄ alkoxy, halo or haloC₁₋₄ alkyl;
Y' is H, C₁₋₄ alkyl, C₁₋₄ alkoxy, halo, haloC₁₋₄ alkyl or NO₂;
Y is H, C₁₋₄ alkyl, halo, halo-C₁₋₄-alkyl or NO₂; and
Z and Z' are independently H or halo.

3. The compound of claim 1, wherein:
R² is H, or C₁₋₄ alkyl;
R³ and R³' are independently H, C₁₋₄ alkyl, C₁₋₄ alkoxy, or halo;
R⁴ is H or C₁₋₄ alkyl;
W¹ is C—Z';
W² is C—Y';
W³ is C—X;
X is H, C₁₋₄ alkyl, C₁₋₄ alkoxy, halo or haloC₁₋₄ alkyl;
Y' is H, C₁₋₄ alkyl, C₁₋₄ alkoxy, halo, or haloC₁₋₄ alkyl;
Y is H, C₁₋₄ alkyl, halo, halo-C₁₋₄-alkyl or NO₂; and
Z and Z' are independently H or halo.

4. The compound of claim 1, wherein:
R² is H, or C₁₋₄ alkyl;
R³ and R³' are independently H, C₁₋₄ alkoxy, or halo;
R⁴ is H or C₁₋₄ alkyl;
W¹ is C—Z';
W² is C—Y';
W³ is C—X;
X is H, C₁₋₄ alkyl, halo or haloC₁₋₄ alkyl;
Y and Y' are independently H, C₁₋₄ alkyl, halo, or haloC₁₋₄ alkyl; and
Z and Z' are independently H or halo.

5. The compound of claim 1, wherein:
R² is H, or C₁₋₄ alkyl;
R³ and R³' are independently H or halo;
R⁴ is H or C₁₋₄ alkyl;
W¹ is C—Z';
W² is C—Y';
W³ is C—X;
X is H, halo or haloC₁₋₄ alkyl;
Y and Y' are independently H, halo, or haloC₁₋₄ alkyl; and
Z and Z' are independently H or halo.

48

6. The compound of claim 1, wherein:
R² is H, methyl or ethyl;
R³ and R³' are H;
R⁴ is H;
W¹ is C—Z';
W² is C—Y';
W³ is C—X;
X is H, Br, Cl, F or CF₃;
Y and Y' are independently H, Br, Cl, F or CF₃; and
Z and Z' are independently H, Br, Cl or F.

7. The compound of claim 1, or a stereoisomer or pharmaceutically acceptable salt from thereof, wherein the compound is selected from:
racemic 2-(3-chlorophenyl)-2H-chromene-3-carboxylic acid
racemic 2-(4-chloro-3-(trifluoromethyl)phenyl)-2H-chromene-3-carboxylic acid
racemic 2-(4-chlorophenyl)-2H-chromene-3-carboxylic acid;
racemic 2-(4-methoxyphenyl)-2H-chromene-3-carboxylic acid;
racemic 2-(3,5-dichlorophenyl)-2H-chromene-3-carboxylic acid;
racemic 2-(3,4-dichlorophenyl)-2-methyl-2H-chromene-3-carboxylic acid;
racemic 2-(3,4-dichlorophenyl)-2-ethyl-2H-chromene-3-carboxylic acid;
racemic 2-(3,4-dichlorophenyl)-2H-chromene-3-carboxylic acid;
racemic 2-(4-chloronaphthalen-l-yl)-2H-chromene-3-carboxylic acid;
racemic 2-(naphthalen-2-yl)-2H-chromene-3-carboxylic acid;
racemic 2-(naphthalen-l-yl)-2H-chromene-3-carboxylic acid;
racemic 2-(3-fluorophenyl)-2H-chromene-3-carboxylic acid;
racemic 2-(3-fluoro-4-chlorophenyl)-2H-chromene-3-carboxylic acid;
racemic 2-(3-chloro-4-fluorophenyl)-2H-chromene-3-carboxylic acid;
racemic 2-(3-trifluoromethylphenyl)-2H-chromene-3-carboxylic acid;
racemic 2-(4-trifluoromethylphenyl)-2H-chromene-3-carboxylic acid;
racemic 2-(3,4-difluorophenyl)-2H-chromene-3-carboxylic acid;
racemic 2-(3-nitrophenyl)-2H-chromene-3-carboxylic acid;
racemic 2-(3-nitro-4-chlorophenyl)-2H-chromene-3-carboxylic acid;
racemic 2-(3-methyl-4-chlorophenyl)-2H-chromene-3-carboxylic acid;
racemic 2-(4-bromophenyl)-2H-chromene-3-carboxylic acid
racemic 2-(3-bromophenyl)-2H-chromene-3-carboxylic acid;
racemic 2-(3,4-dibromophenyl)-2H-chromene-3-carboxylic acid;
racemic 2-(3-fluoro-4-trifluoromethylphenyl)-2H-chromene-3-carboxylic acid;
racemic 2-(4-methylphenyl)-2H-chromene-3-carboxylic acid;
racemic 2-(3-methylphenyl)-2H-chromene-3-carboxylic acid;
racemic 2(3-trifluoromethyl-4-fluoro-phenyl)-2H-chromene-3-carboxylic acid;

racemic 2-(2,3-dichlorophenyl)-2H-chromene-3-carboxylic acid;
(−)-2-(3,4-dichlorophenyl)-2H-chromene-3-carboxylic acid;
(+)-2-(3,4-dichlorophenyl)-2H-chromene-3-carboxylic acid;
racemic 2-(3-methoxy-4-chlorophenyl)-2H-chromene-3-carboxylic acid;
racemic 2-(3-bromo-4-chlorophenyl)-2H-chromene-3-carboxylic acid;
racemic 2-(3-chloro-4-trifluoromethyl-phenyl)-2H-chromene-3-carboxylic acid;
2-(3,4-dichlorophenyl)-6-methoxy-2H-chromene-3-carboxylic acid;
racemic 2(3,4-dichlorophenyl)-7-fluoro-2H-chromene-3-carboxylic acid;
racemic 2-(3,4-dichlorophenyl)-6-chloro-2H-chromene-3-carboxylic acid;
racemic 2-(3,4-dichlorophenyl)-6-fluoro-2H-chromene-3-carboxylic acid;
racemic 2-(3,4-dichlorophenyl)-7-bromo-2H-chromene-3-carboxylic acid; and
racemic 2(3,4-dichlorophenyl)-7-methoxy-2H-chromene-3-carboxylic acid.

8. A pharmaceutical composition comprised of a pharmaceutically acceptable carrier and a compound of claim 1.

* * * * *